US010106592B2

(12) United States Patent
Merchant

(10) Patent No.: US 10,106,592 B2
(45) Date of Patent: Oct. 23, 2018

(54) INTERLEUKIN-4 RECEPTOR-BINDING FUSION PROTEINS AND USES THEREOF

(71) Applicant: Medicenna Therapeutics, Inc., Vancouver (CA)

(72) Inventor: Fahar Merchant, Vancouver (CA)

(73) Assignee: Medicenna Therapeutics Inc., Toronto, Ontario ( * ) Notice: Subject to any disclaimer, the term of this patent is extended or adjusted under 35 U.S.C. 154(b) by 99 days.

(21) Appl. No.: 15/024,787

(22) PCT Filed: Sep. 24, 2014

(86) PCT No.: PCT/CA2014/050916

§ 371 (c)(1),
(2) Date: Mar. 24, 2016

(87) PCT Pub. No.: WO2015/042706

PCT Pub. Date: Apr. 2, 2015

(65) Prior Publication Data

US 2016/0237135 A1 Aug. 18, 2016

Related U.S. Application Data

(60) Provisional application No. 61/881,930, filed on Sep. 24, 2013.

(51) Int. Cl.

| | |
|---|---|
| ***A61K 38/17*** | (2006.01) |
| ***A61K 38/20*** | (2006.01) |
| ***C07K 14/54*** | (2006.01) |
| ***C07K 14/47*** | (2006.01) |
| ***C07K 19/00*** | (2006.01) |
| ***C12N 5/10*** | (2006.01) |
| ***C12N 15/63*** | (2006.01) |
| ***C12N 5/071*** | (2010.01) |
| ***A61K 38/19*** | (2006.01) |
| ***C12N 5/0783*** | (2010.01) |
| *A61K 38/00* | (2006.01) |

(52) U.S. Cl.

CPC ...... *C07K 14/5406* (2013.01); *A61K 38/1761* (2013.01); *A61K 38/193* (2013.01); *A61K 38/2026* (2013.01); *C07K 14/4747* (2013.01); *C12N 5/0602* (2013.01); *C12N 5/0636* (2013.01); *C12N 15/63* (2013.01); *A61K 38/00* (2013.01); *C07K 2319/00* (2013.01); *C12N 2501/48* (2013.01)

(58) Field of Classification Search

CPC ............ A61K 2300/00; A61K 38/2026; A61K 38/1761; A61K 38/17; A61K 38/20; A61K 38/2086; C07K 14/54; C07K 14/5406; C07K 14/5437; C07K 14/4747; C07K 2319/00

See application file for complete search history.

(56) References Cited

U.S. PATENT DOCUMENTS

| | | | | |
|---|---|---|---|---|
| 6,011,002 | A | 1/2000 | Pastan et al. | |
| 6,737,511 | B1 | 5/2004 | Youle et al. | |
| 9,512,194 | B2 * | 12/2016 | Garcia | C07K 14/5437 |
| 2005/0106148 | A1 | 5/2005 | Kay et al. | |
| 2010/0183545 | A1 | 7/2010 | Puri | |
| 2010/0317577 | A1 * | 12/2010 | Youle | C07K 14/4747 514/7.6 |

FOREIGN PATENT DOCUMENTS

| | | | | |
|---|---|---|---|---|
| WO | WO 01/34645 | A2 | | 5/2001 |
| WO | WO 2006/074451 | A2 | | 7/2006 |
| WO | WO 2009/029601 | A2 | | 3/2009 |
| WO | WO 2010/031185 | A1 | | 3/2010 |
| WO | WO 2012/054929 | A2 | | 4/2012 |
| WO | WO-2012054929 | A2 | * | 4/2012 |
| WO | WO 2012/139112 | A1 | | 10/2012 |
| WO | WO 2013/112871 | A1 | | 8/2013 |

OTHER PUBLICATIONS

Bhatia et al. Innovative approaches for enhancing cancer gene therapy.*
Juengst, E.T. What next for human gene therapy? BMJ 326: 1410-1411, 2003.*
Junttila et al. Redirecting cell-type specific cytokine responses with engineered interleukin-4 superkines. Nature Chemical Biol 8: 990-998, 2012.*
Phillips, A.J. The challenge of gene therapy and DNA delivery. J Pharmacy and Pharmacol 53: 1169-1174, 2001.*
Rubanyi, G.M. The future of human gene therapy. Molecular Aspects Med 22:113-142, 2001.*
Murray, E.J. "Cloning Genes in Mammalian Cell-lines" in Molecular Biology and Biotechnology. Great Britain: The Royal Society of Chemistry, 2000, pp. 177-201.*
Bhatia et al. Innovative approaches for enhancing cancer gene therapy. Discovery Med 15(84): 309-317, 2013.*
Cao et al. In vivo delivery of a Bcl-xl fusion protein containing the TAT protein transduction domain protects against ischemic brain injury and neuronal apoptosis. J Neurosci 22(13): 5423-5431, 2002.*
Hotchkiss et al. TAT-BH4 and TAT-Bcl-xl peptides protect against sepsis-induced lymphocyte apoptosis in vivo. J Immunol 176: 5471-5477, 2006.*
Bachran et al. "Anthrax Toxin-Mediated Delivery of the Pseudomonas Exotoxin A Enzymatic Domain to the Cytosol of Tumor Cells via Cleavable Ubiquitin Fusions" mBio vol. 4, pp. 201-213 (2013).
Boise et al. "bcl-x, a bcl-2-Related Gene That Functions as a Dominant Regulator of Apoptotic Cell Death" Cell, vol. 74, pp. 597-608 (1993).
Cleary et al "Cloning and structural analysis of cDNAs for bcl-2 and a hybrid bcl-2/immunoglobulin transcript resulting from the t(14;18) translocation" Cell Press, vol. 47, No. 1, pp. 19-28 (1986).

(Continued)

*Primary Examiner* — Bridget E Bunner

(74) *Attorney, Agent, or Firm* — Morgan Lewis & Bockius LLP; Christina A. MacDougall

(57) ABSTRACT

The present invention relates to interleukin-4 receptor-binding fusion proteins. More specifically, the invention provides, in part, fusion proteins that include an interleukin-4 or interleukin-13 protein moiety joined to an anti-apoptotic Bcl-2 family member protein moiety.

16 Claims, 9 Drawing Sheets

Specification includes a Sequence Listing.

(56) References Cited

OTHER PUBLICATIONS

Diehn et al. "Cancer Stem Cells and Radiotherapy: New Insights Into Tumor Radioresistance" Journal of National Cancer Institute, vol. 98, pp. 1755-1757 (2006).
GenBank Accession No. Q07817, bcl gene apotosis [homo sapiens] Feb. 28, 2018.
GenBank Accession No. Z23115, bcl XL gene [homo sapiens] Oct. 7, 2008.
Kreitman et al. "Recombinant Toxins Containing Human Granulocyte-Macrophage Colony-Stimulating Factor and Either Pseudomonas Exotoxin or Diphtheria Toxin Kill Gastrointestinal Cancer and Leukemia Cells" Blood vol. 90, pp. 252-259 (1997).
Laske et al. "Tumor regression with regional distribution of the targeted toxin TF-CRM107 in patients with malignant brain tumors" Nature, vol. 3, pp. 1362-1368 (1997).
Lomonosova and Chinnadurai "BH3-only proteins in apoptosis and beyond: an overview" Oncogene, vol. 27, pp. S2-S19 (2009).
Rubin "Neuronal cell death: when, why and how" British Medical Bulletin, vol. 53, Issue 3, pp. 617-631 (1997).
Sakariassen et al. "Cancer Stem Cells as Mediators of Treatment Resistance in Brain Tumors: Status and Controversies" Neoplasia, vol. 9, No. 11, pp. 882-892 (2007).
Shimamura et al. "Interleukin-4 Cytotoxin Therapy Synergizes with Gemcitabine in a Mouse Model of Pancreatic Ductal Adenocarcinoma" Cancer Research, vol. 67, pp. 9903-9912 (2007).
Suga et al. "Transplant Immunosuppression Enhances Efficiency of Adenoviral-Mediated Gene Retransfection: Inhibition of Interferon-y and Immunoglobin G" The Society of Thoracic Surgeons, vol. 73, pp. 1092-1097 (2002).
Thorpe et al. "Toxicity of diphtheria toxin for lymphoblastoid cells is increased by conjugation to antilymphocytic globulin" Nature, vol. 271, pp. 752-755 (1978).
Tsujimoto and Croce "Analysis of the structure, transcripts, and protein products of bcl-2, the gene involved in human follicular lymphoma" Proc. Natl. Acad. Sci., vol. 83, pp. 5214-5218 (1986).
White "Life, Death, and the Pursuit of Apoptosis" Genes and Development 10, pp. 1-15 (1996).
Yang et al. "Bad, a heterodimeric partner for Bcl-XL and Bcl-2, displaces Bax and promotes cell death" Cell, vol. 80, pp. 285-291 (1995).
Youle et al. "Receptor-mediated uptake of an extracellular Bcl-xL fusion protein inhibits apoptosis" Proceedings of Nat'l Academy of Sciences, vol. 96, pp. 9563-9567 (1999).
Youle et al. "The Cytokine, Granulocyte-Macrophage Colony-stimulating Factor (GM-CSF), Can Deliver Bcl-XL as an Extracellular Fusion Protein to Protect Cells from Apoptosis and Retain Differentiation Induction" The Journal of Biological Chemistry, vol. 282, No. 15, pp. 11246-11254 (2007).

* cited by examiner

A. cpIL4-BclxL nucleic acid sequence:

ATGGACACGACTGAGAAAGAGACCTTCTGCCGTGCAGCAACTGTTCTGCGTCAGTTCTATTCCCACCACGAAAAAG
ATACGCGTTGCCTGGGTGCTACTGCGCAGCAGTTCCATCGTCATAAGCAACTGATTCGCTTTCTGAAACGTCTGGA
CCGTAACCTGTGGGGTCTGGCCGGTCTGAACAGCTGCCCGGTCAAAGAAGCGAACCAGTCCACTCTGGAAAACTT
CCTGGAACGCCTGAAGACCATCATGCGCGAAAAATACTCCAAGTGTTCCAGCGGCGGCAACGGCGGTCACAAATG
TGACATCACCCTGCAGGAAATCATCAAAACTCTGAATTCTCTGACTGAGCAGAAAACCCTGTGTACCGAACTGACC
GTGACCGATATTTTTGCCGCTTCTAAAGCGTCTGGTGGCCCGGAATCTCAGTCTAACCGCGAACTGGTGGTGGACT
TCCTGTCTTATAAACTGAGCCAGAAAGGCTACTCCTGGAGCCAGTTCAGCGACGTAGAGGAGAACCGTACCGAAG
CTCCTGAAGGCACCGAGAGCGAGATGGAAACCCCATCCGCGATTAACGGCAACCCGTCCTGGCACCTGGCTGATT
CTCCGGCGGTAAACGGCGCAACTGGTCATTCTAGCTCCCTGGATGCACGTGAAGTAATCCCGATGGCCGCGGTTA
AACAGGCGCTGCGTGAAGCTGGTGACGAATTTGAGCTGCGCTACCGCCGTGCATTTTCTGATCTGACCTCCCAGCT
GCACATCACGCCGGGTACCGCATACCAAAGCTTCGAACAGGTGGTTAACGAACTGTTTCGTGACGGCGTCAACTG
GGGCCGCATCGTGGCCTTTTTCTCTTTCGGCGGTGCCCTGTGCGTCGAATCTGTTGACAAAGAAATGCAGGTTCTG
GTGAGCCGTATTGCGGCTTGGATGGCAACTTATCTGAACGATCACCTGGAACCGTGGATCCAGGAAAACGGTGGT
TGGGATACCTTCGTTGAACTGTACGGTAACAATGCTGCGGCGGAATCCCGTAAGGGTCAAGAACGTTTCAATCGC
TGGTTCCTGACCGGCATGACTGTTGCTGGTGTAGTTCTGCTGGGTTCTCTGTTCTCCCGTAAA (SEQ ID NO : 30).

B. cpIL4-BclxL amino acid sequence:

MDTTEKETFCRAATVLRQFYSHHEKDTRCLGATAQQFHRHKQLIRFLKRLDRNLWGLAGLNSCPVKEANQSTLENFLER
LKTIMREKYSKCSSGGNGGHKCDITLQEIIKTLNSLTEQKTLCTELTVTDIFAASKASGGPESQSNRELVVDFLSYKLSQKGY
SWSQFSDVEENRTEAPEGTESEMETPSAINGNPSWHLADSPAVNGATGHSSSLDAREVIPMAAVKQALREAGDEFEL
RYRRAFSDLTSQLHITPGTAYQSFEQVVNELFRDGVNWGRIVAFFSFGGALCVESVDKEMQVLVSRIAAWMATYLND
HLEPWIQENGGWDTFVELYGNNAAAESRKGQERFNRWFLTGMTVAGVVLLGSLFSRK (SEQ ID NO: 18).

FIGURE 4

C. cpIL4-Ub-BclxL nucleic acid sequence:

ATGGACACGACTGAGAAAGAGACCTTCTGCCGTGCAGCAACTGTTCTGCGTCAGTTCTATTCCCACCACGAAAAAG
ATACGCGTTGCCTGGGTGCTACTGCGCAGCAGTTCCATCGTCATAAGCAACTGATTCGCTTTCTGAAACGTCTGGA
CCGTAACCTGTGGGGTCTGGCCGGTCTGAACAGCTGCCCGGTCAAAGAAGCGAACCAGTCCACTCTGGAAAACTT
CCTGGAACGCCTGAAGACCATCATGCGCGAAAAATACTCCAAGTGTTCCAGCGGCGGCAACGGCGGTCACAAATG
TGACATCACCCTGCAGGAAATCATCAAAACTCTGAATTCTCTGACTGAGCAGAAAACCCTGTGTACCGAACTGACC
GTGACCGATATTTTTGCCGCTTCTAAAGGTGGCGGCTCTATGCAAATTTTCGTTCGTACCCTGACGGGTCGTACCAT
CACTCTGGAAGTAGAACCGAGCGACACGATCGAAAATGTCCGCGCACGCATCCAAGACCGCGAAGGCATTCCACC
GGATCAGCAGCGTCTGATCTTCGCCGGTCGCCAGCTGGAGGATGGTCGTACTCTGTCCGATTATAACATCCAGCGT
GAATCCACCCTGCACCTGGTGCTGCGTCTGCGTGGCGGTGGTAGCTCTCAGTCTAACCGCGAACTGGTGGTGGAC
TTCCTGTCTTATAAACTGAGCCAGAAAGGCTACTCCTGGAGCCAGTTCAGCGACGTAGAGGAGAACCGTACCGAA
GCTCCTGAAGGCACCGAGAGCGAGATGGAAACCCCATCCGCGATTAACGGCAACCCGTCCTGGCACCTGGCTGAT
TCTCCGGCGGTAAACGGCGCAACTGGTCATTCTAGCTCCCTGGATGCACGTGAAGTAATCCCGATGGCCGCGGTT
AAACAGGCGCTGCGTGAAGCTGGTGACGAATTTGAGCTGCGCTACCGCCGTGCATTTTCTGATCTGACCTCCCAGC
TGCACATCACGCCGGGTACCGCATACCAAAGCTTCGAACAGGTGGTTAACGAACTGTTTCGTGACGGCGTCAACT
GGGGCCGCATCGTGGCCTTTTTCTCTTTCGGCGGTGCCCTGTGCGTCGAATCTGTTGACAAAGAAATGCAGGTTCT
GGTGAGCCGTATTGCGGCTTGGATGGCAACTTATCTGAACGATCACCTGGAACCGTGGATCCAGGAAAACGGTGG
TTGGGATACCTTCGTTGAACTGTACGGTAACAATGCTGCGGCGGAATCCCGTAAGGGTCAAGAACGTTTCAATCG
CTGGTTCCTGACCGGCATGACTGTTGCTGGTGTAGTTCTGCTGGGTTCTCTGTTCTCCCGTAAA (SEQ ID NO: 31).

D. cpIL4-Ub-BclxL amino acid sequence:

MDTTEKETFCRAATVLRQFYSHHEKDTRCLGATAQQFHRHKQLIRFLKRLDRNLWGLAGLNSCPVKEANQSTLENFLER
LKTIMREKYSKCSSGGNGGHKCDITLQEIIKTLNSLTEQKTLCTELTVTDIFAASKGGGSMQIFVRTLTGRTITLEVEPSDTIE
NVRARIQDREGIPPDQQRLIFAGRQLEDGRTLSDYNIQRESTLHLVLRLRGGGSSQSNRELVVDFLSYKLSQKGYSWSQF
SDVEENRTEAPEGTESEMETPSAINGNPSWHLADSPAVNGATGHSSSLDAREVIPMAAVKQALREAGDEFELRYRRAF
SDLTSQLHITPGTAYQSFEQVVNELFRDGVNWGRIVAFFSFGGALCVESVDKEMQVLVSRIAAWMATYLNDHLEPWI
QENGGWDTFVELYGNNAAAESRKGQERFNRWFLTGMTVAGVVLLGSLFSRK (SEQ ID NO: 20).

FIGURE 4 contd.

SEQUENCE LISTING

```
<160> NUMBER OF SEQ ID NOS: 31

<210> SEQ ID NO 1
<211> LENGTH: 130
<212> TYPE: PRT
<213> ORGANISM: Artificial Sequence
<220> FEATURE:
<223> OTHER INFORMATION: IL-4 sequence including an additional
      methionine at the N-terminus

<400> SEQUENCE: 1

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130


<210> SEQ ID NO 2
<211> LENGTH: 130
<212> TYPE: PRT
<213> ORGANISM: Artificial Sequence
<220> FEATURE:
<223> OTHER INFORMATION: IL-4 sequence including an additional
      methionine at the N-terminus

<400> SEQUENCE: 2

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asp Thr Thr Glu Lys Glu Thr Phe Cys Arg
        35                  40                  45

Ala Ala Thr Val Leu Arg Gln Phe Tyr Ser His His Glu Lys Asp Thr
```

```
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130


<210> SEQ ID NO 3
<211> LENGTH: 134
<212> TYPE: PRT
<213> ORGANISM: Artificial Sequence
<220> FEATURE:
<223> OTHER INFORMATION: circularly permuted IL-4 sequence

<400> SEQUENCE: 3

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser
    130


<210> SEQ ID NO 4
<211> LENGTH: 134
<212> TYPE: PRT
<213> ORGANISM: Artificial Sequence
<220> FEATURE:
<223> OTHER INFORMATION: circularly permuted “RGA” variant IL-4

<400> SEQUENCE: 4

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80
```

```
Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser
    130


<210> SEQ ID NO 5
<211> LENGTH: 134
<212> TYPE: PRT
<213> ORGANISM: Artificial Sequence
<220> FEATURE:
<223> OTHER INFORMATION: circularly permuted “KFR” variant IL-4

<400> SEQUENCE: 5

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser
    130


<210> SEQ ID NO 6
<211> LENGTH: 133
<212> TYPE: PRT
<213> ORGANISM: Artificial Sequence
<220> FEATURE:
<223> OTHER INFORMATION: circularly permuted “KF” variant IL-4

<400> SEQUENCE: 6

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Lys Cys Ser Ser Gly Gly Asn Gly
                85                  90                  95

Gly His Lys Cys Asp Ile Thr Leu Gln Glu Ile Ile Lys Thr Leu Asn
            100                 105                 110
```

-continued

```
Ser Leu Thr Glu Gln Lys Thr Leu Cys Thr Glu Leu Thr Val Thr Asp
        115                 120                 125

Ile Phe Ala Ala Ser
    130


<210> SEQ ID NO 7
<211> LENGTH: 114
<212> TYPE: PRT
<213> ORGANISM: Artificial Sequence
<220> FEATURE:
<223> OTHER INFORMATION: IL-13 including an additional methionine at the
      N-terminus

<400> SEQUENCE: 7

Met Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Gln
            100                 105                 110

Phe Asn


<210> SEQ ID NO 8
<211> LENGTH: 114
<212> TYPE: PRT
<213> ORGANISM: Artificial Sequence
<220> FEATURE:
<223> OTHER INFORMATION: " A11" IL-13 variant

<400> SEQUENCE: 8

Met Pro Gly Pro Val Pro Pro Ser Thr Ala Val Arg Glu Leu Ile Glu
1               5                   10                  15

Glu Leu Ile Asn Ile Thr Gln Asn Gln Lys Ala Pro Leu Cys Asn Gly
            20                  25                  30

Ser Met Val Trp Ser Ile Asn Arg Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Ser Ser Lys Ile Glu Val Ala Gln Phe
                85                  90                  95

Val Lys Asp Leu Leu Phe His Leu Arg Thr Leu Phe Arg Glu Gly Gln
            100                 105                 110

Phe Asn


<210> SEQ ID NO 9
<211> LENGTH: 114
<212> TYPE: PRT
<213> ORGANISM: Artificial Sequence
```

<220> FEATURE:
<223> OTHER INFORMATION: "DN" IL-13 variant

<400> SEQUENCE: 9

```
Met Pro Gly Pro Val Pro Pro Ser Thr Ala Val Arg Ala Leu Ile Glu
1               5                   10                  15

Glu Leu Ile Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Asp Met Leu Ser Gly Phe Cys Pro His Lys Val Ser Ala Gly Gln
65                  70                  75                  80

Phe Ser Ser Leu His Val Arg Ser Ser Lys Ile Glu Val Ala Gln Phe
                85                  90                  95

Val Lys Asp Leu Leu Phe His Leu Arg Thr Leu Phe Arg Glu Gly Gln
            100                 105                 110

Phe Asn
```

<210> SEQ ID NO 10
<211> LENGTH: 117
<212> TYPE: PRT
<213> ORGANISM: Artificial Sequence
<220> FEATURE:
<223> OTHER INFORMATION: circularly permuted IL-13

<400> SEQUENCE: 10

```
Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Asp Thr Lys Ile
        35                  40                  45

Glu Val Ala Gln Phe Val Lys Asp Leu Leu Leu His Leu Lys Lys Leu
    50                  55                  60

Phe Arg Glu Gly Gln Phe Asn Gly Gly Ser Gly Pro Gly Pro Val Pro
65                  70                  75                  80

Pro Ser Thr Ala Leu Arg Glu Leu Ile Glu Glu Leu Val Asn Ile Thr
                85                  90                  95

Gln Asn Gln Lys Ala Pro Leu Cys Asn Gly Ser Met Val Trp Ser Ile
            100                 105                 110

Asn Leu Thr Ala Gly
        115
```

<210> SEQ ID NO 11
<211> LENGTH: 118
<212> TYPE: PRT
<213> ORGANISM: Artificial Sequence
<220> FEATURE:
<223> OTHER INFORMATION: circularly permuted IL-13

<400> SEQUENCE: 11

```
Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Asp Thr Lys Ile
```

35 40 45

Glu Val Ala Gln Phe Val Lys Asp Leu Leu Leu His Leu Lys Lys Leu
50 55 60

Phe Arg Glu Gly Gln Phe Asn Gly Gly Ser Gly Met Pro Gly Pro Val
65 70 75 80

Pro Pro Ser Thr Ala Leu Arg Glu Leu Ile Glu Glu Leu Val Asn Ile
85 90 95

Thr Gln Asn Gln Lys Ala Pro Leu Cys Asn Gly Ser Met Val Trp Ser
100 105 110

Ile Asn Leu Thr Ala Gly
115

<210> SEQ ID NO 12
<211> LENGTH: 117
<212> TYPE: PRT
<213> ORGANISM: Artificial Sequence
<220> FEATURE:
<223> OTHER INFORMATION: circularly permuted IL-13 “A11” variant

<400> SEQUENCE: 12

Met Tyr Cys Ala Ala Leu Glu Ser Leu Ile Asn Val Ser Gly Cys Ser
1 5 10 15

Ala Ile Glu Lys Thr Gln Arg Met Leu Ser Gly Phe Cys Pro His Lys
20 25 30

Val Ser Ala Gly Gln Phe Ser Ser Leu His Val Arg Ser Ser Lys Ile
35 40 45

Glu Val Ala Gln Phe Val Lys Asp Leu Leu Phe His Leu Arg Thr Leu
50 55 60

Phe Arg Glu Gly Gln Phe Asn Gly Gly Ser Gly Pro Gly Pro Val Pro
65 70 75 80

Pro Ser Thr Ala Val Arg Glu Leu Ile Glu Glu Leu Ile Asn Ile Thr
85 90 95

Gln Asn Gln Lys Ala Pro Leu Cys Asn Gly Ser Met Val Trp Ser Ile
100 105 110

Asn Arg Thr Ala Gly
115

<210> SEQ ID NO 13
<211> LENGTH: 118
<212> TYPE: PRT
<213> ORGANISM: Artificial Sequence
<220> FEATURE:
<223> OTHER INFORMATION: circularly permuted IL-13

<400> SEQUENCE: 13

Met Tyr Cys Ala Ala Leu Glu Ser Leu Ile Asn Val Ser Gly Cys Ser
1 5 10 15

Ala Ile Glu Lys Thr Gln Arg Met Leu Ser Gly Phe Cys Pro His Lys
20 25 30

Val Ser Ala Gly Gln Phe Ser Ser Leu His Val Arg Ser Ser Lys Ile
35 40 45

Glu Val Ala Gln Phe Val Lys Asp Leu Leu Phe His Leu Arg Thr Leu
50 55 60

Phe Arg Glu Gly Gln Phe Asn Gly Gly Ser Gly Met Pro Gly Pro Val
65 70 75 80

Pro Pro Ser Thr Ala Val Arg Glu Leu Ile Glu Glu Leu Ile Asn Ile
85 90 95

-continued

```
Thr Gln Asn Gln Lys Ala Pro Leu Cys Asn Gly Ser Met Val Trp Ser
            100                 105                 110

Ile Asn Arg Thr Ala Gly
        115


<210> SEQ ID NO 14
<211> LENGTH: 117
<212> TYPE: PRT
<213> ORGANISM: Artificial Sequence
<220> FEATURE:
<223> OTHER INFORMATION: circularly permuted "DN" IL-13

<400> SEQUENCE: 14

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Pro Gly Pro Val Pro
65                  70                  75                  80

Pro Ser Thr Ala Val Arg Ala Leu Ile Glu Glu Leu Ile Asn Ile Thr
                85                  90                  95

Gln Asn Gln Lys Ala Pro Leu Cys Asn Gly Ser Met Val Trp Ser Ile
            100                 105                 110

Asn Leu Thr Ala Gly
        115


<210> SEQ ID NO 15
<211> LENGTH: 118
<212> TYPE: PRT
<213> ORGANISM: Artificial Sequence
<220> FEATURE:
<223> OTHER INFORMATION: circularly permuted IL-13

<400> SEQUENCE: 15

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Met Pro Gly Pro Val
65                  70                  75                  80

Pro Pro Ser Thr Ala Val Arg Ala Leu Ile Glu Glu Leu Ile Asn Ile
                85                  90                  95

Thr Gln Asn Gln Lys Ala Pro Leu Cys Asn Gly Ser Met Val Trp Ser
            100                 105                 110

Ile Asn Leu Thr Ala Gly
        115


<210> SEQ ID NO 16
<211> LENGTH: 232
<212> TYPE: PRT
<213> ORGANISM: Homom sapiens
```

<400> SEQUENCE: 16

Ser Gln Ser Asn Arg Glu Leu Val Val Asp Phe Leu Ser Tyr Lys Leu
1               5                   10                  15

Ser Gln Lys Gly Tyr Ser Trp Ser Gln Phe Ser Asp Val Glu Glu Asn
            20                  25                  30

Arg Thr Glu Ala Pro Glu Gly Thr Glu Ser Glu Met Glu Thr Pro Ser
        35                  40                  45

Ala Ile Asn Gly Asn Pro Ser Trp His Leu Ala Asp Ser Pro Ala Val
    50                  55                  60

Asn Gly Ala Thr Gly His Ser Ser Ser Leu Asp Ala Arg Glu Val Ile
65                  70                  75                  80

Pro Met Ala Ala Val Lys Gln Ala Leu Arg Glu Ala Gly Asp Glu Phe
                85                  90                  95

Glu Leu Arg Tyr Arg Arg Ala Phe Ser Asp Leu Thr Ser Gln Leu His
            100                 105                 110

Ile Thr Pro Gly Thr Ala Tyr Gln Ser Phe Glu Gln Val Val Asn Glu
        115                 120                 125

Leu Phe Arg Asp Gly Val Asn Trp Gly Arg Ile Val Ala Phe Phe Ser
    130                 135                 140

Phe Gly Gly Ala Leu Cys Val Glu Ser Val Asp Lys Glu Met Gln Val
145                 150                 155                 160

Leu Val Ser Arg Ile Ala Ala Trp Met Ala Thr Tyr Leu Asn Asp His
                165                 170                 175

Leu Glu Pro Trp Ile Gln Glu Asn Gly Gly Trp Asp Thr Phe Val Glu
            180                 185                 190

Leu Tyr Gly Asn Asn Ala Ala Ala Glu Ser Arg Lys Gly Gln Glu Arg
        195                 200                 205

Phe Asn Arg Trp Phe Leu Thr Gly Met Thr Val Ala Gly Val Val Leu
    210                 215                 220

Leu Gly Ser Leu Phe Ser Arg Lys
225                 230

<210> SEQ ID NO 17
<211> LENGTH: 7
<212> TYPE: PRT
<213> ORGANISM: Artificial Sequence
<220> FEATURE:
<223> OTHER INFORMATION: linker

<400> SEQUENCE: 17

Lys Ala Ser Gly Gly Pro Glu
1               5

<210> SEQ ID NO 18
<211> LENGTH: 373
<212> TYPE: PRT
<213> ORGANISM: Artificial Sequence
<220> FEATURE:
<223> OTHER INFORMATION: cpIL-4-BclxL

<400> SEQUENCE: 18

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Lys Ala Ser Gly Gly Pro Glu Ser Gln Ser
    130                 135                 140

Asn Arg Glu Leu Val Val Asp Phe Leu Ser Tyr Lys Leu Ser Gln Lys
145                 150                 155                 160

Gly Tyr Ser Trp Ser Gln Phe Ser Asp Val Glu Glu Asn Arg Thr Glu
                165                 170                 175

Ala Pro Glu Gly Thr Glu Ser Glu Met Glu Thr Pro Ser Ala Ile Asn
            180                 185                 190

Gly Asn Pro Ser Trp His Leu Ala Asp Ser Pro Ala Val Asn Gly Ala
        195                 200                 205

Thr Gly His Ser Ser Ser Leu Asp Ala Arg Glu Val Ile Pro Met Ala
    210                 215                 220

Ala Val Lys Gln Ala Leu Arg Glu Ala Gly Asp Glu Phe Glu Leu Arg
225                 230                 235                 240

Tyr Arg Arg Ala Phe Ser Asp Leu Thr Ser Gln Leu His Ile Thr Pro
                245                 250                 255

Gly Thr Ala Tyr Gln Ser Phe Glu Gln Val Val Asn Glu Leu Phe Arg
            260                 265                 270

Asp Gly Val Asn Trp Gly Arg Ile Val Ala Phe Phe Ser Phe Gly Gly
        275                 280                 285

Ala Leu Cys Val Glu Ser Val Asp Lys Glu Met Gln Val Leu Val Ser
    290                 295                 300

Arg Ile Ala Ala Trp Met Ala Thr Tyr Leu Asn Asp His Leu Glu Pro
305                 310                 315                 320

Trp Ile Gln Glu Asn Gly Gly Trp Asp Thr Phe Val Glu Leu Tyr Gly
                325                 330                 335

Asn Asn Ala Ala Ala Glu Ser Arg Lys Gly Gln Glu Arg Phe Asn Arg
            340                 345                 350

Trp Phe Leu Thr Gly Met Thr Val Ala Gly Val Val Leu Leu Gly Ser
        355                 360                 365

Leu Phe Ser Arg Lys
    370

<210> SEQ ID NO 19
<211> LENGTH: 82
<212> TYPE: PRT
<213> ORGANISM: Artificial Sequence
<220> FEATURE:
<223> OTHER INFORMATION: ubiquitin linker

<400> SEQUENCE: 19

Gly Gly Gly Ser Met Gln Ile Phe Val Arg Thr Leu Thr Gly Arg Thr
1               5                   10                  15

Ile Thr Leu Glu Val Glu Pro Ser Asp Thr Ile Glu Asn Val Arg Ala
            20                  25                  30

Arg Ile Gln Asp Arg Glu Gly Ile Pro Pro Asp Gln Gln Arg Leu Ile
35 40 45

Phe Ala Gly Arg Gln Leu Glu Asp Gly Arg Thr Leu Ser Asp Tyr Asn
50 55 60

Ile Gln Arg Glu Ser Thr Leu His Leu Val Leu Arg Leu Arg Gly Gly
65 70 75 80

Gly Ser

<210> SEQ ID NO 20
<211> LENGTH: 448
<212> TYPE: PRT
<213> ORGANISM: Artificial Sequence
<220> FEATURE:
<223> OTHER INFORMATION: cpIL-4-Ub-BclxL

<400> SEQUENCE: 20

Met Asp Thr Thr Glu Lys Glu Thr Phe Cys Arg Ala Ala Thr Val Leu
1 5 10 15

Arg Gln Phe Tyr Ser His His Glu Lys Asp Thr Arg Cys Leu Gly Ala
20 25 30

Thr Ala Gln Gln Phe His Arg His Lys Gln Leu Ile Arg Phe Leu Lys
35 40 45

Arg Leu Asp Arg Asn Leu Trp Gly Leu Ala Gly Leu Asn Ser Cys Pro
50 55 60

Val Lys Glu Ala Asn Gln Ser Thr Leu Glu Asn Phe Leu Glu Arg Leu
65 70 75 80

Lys Thr Ile Met Arg Glu Lys Tyr Ser Lys Cys Ser Ser Gly Gly Asn
85 90 95

Gly Gly His Lys Cys Asp Ile Thr Leu Gln Glu Ile Ile Lys Thr Leu
100 105 110

Asn Ser Leu Thr Glu Gln Lys Thr Leu Cys Thr Glu Leu Thr Val Thr
115 120 125

Asp Ile Phe Ala Ala Ser Gly Gly Gly Ser Met Gln Ile Phe Val Arg
130 135 140

Thr Leu Thr Gly Arg Thr Ile Thr Leu Glu Val Glu Pro Ser Asp Thr
145 150 155 160

Ile Glu Asn Val Arg Ala Arg Ile Gln Asp Arg Glu Gly Ile Pro Pro
165 170 175

Asp Gln Gln Arg Leu Ile Phe Ala Gly Arg Gln Leu Glu Asp Gly Arg
180 185 190

Thr Leu Ser Asp Tyr Asn Ile Gln Arg Glu Ser Thr Leu His Leu Val
195 200 205

Leu Arg Leu Arg Gly Gly Gly Ser Ser Gln Ser Asn Arg Glu Leu Val
210 215 220

Val Asp Phe Leu Ser Tyr Lys Leu Ser Gln Lys Gly Tyr Ser Trp Ser
225 230 235 240

Gln Phe Ser Asp Val Glu Glu Asn Arg Thr Glu Ala Pro Glu Gly Thr
245 250 255

Glu Ser Glu Met Glu Thr Pro Ser Ala Ile Asn Gly Asn Pro Ser Trp
260 265 270

His Leu Ala Asp Ser Pro Ala Val Asn Gly Ala Thr Gly His Ser Ser
275 280 285

Ser Leu Asp Ala Arg Glu Val Ile Pro Met Ala Ala Val Lys Gln Ala
290 295 300

```
Leu Arg Glu Ala Gly Asp Glu Phe Glu Leu Arg Tyr Arg Arg Ala Phe
305                 310                 315                 320

Ser Asp Leu Thr Ser Gln Leu His Ile Thr Pro Gly Thr Ala Tyr Gln
                325                 330                 335

Ser Phe Glu Gln Val Val Asn Glu Leu Phe Arg Asp Gly Val Asn Trp
            340                 345                 350

Gly Arg Ile Val Ala Phe Phe Ser Phe Gly Gly Ala Leu Cys Val Glu
        355                 360                 365

Ser Val Asp Lys Glu Met Gln Val Leu Val Ser Arg Ile Ala Ala Trp
    370                 375                 380

Met Ala Thr Tyr Leu Asn Asp His Leu Glu Pro Trp Ile Gln Glu Asn
385                 390                 395                 400

Gly Gly Trp Asp Thr Phe Val Glu Leu Tyr Gly Asn Asn Ala Ala Ala
                405                 410                 415

Glu Ser Arg Lys Gly Gln Glu Arg Phe Asn Arg Trp Phe Leu Thr Gly
            420                 425                 430

Met Thr Val Ala Gly Val Val Leu Leu Gly Ser Leu Phe Ser Arg Lys
        435                 440                 445


<210> SEQ ID NO 21
<211> LENGTH: 448
<212> TYPE: PRT
<213> ORGANISM: Artificial Sequence
<220> FEATURE:
<223> OTHER INFORMATION: cpKRF4-Ub-BclxL

<400> SEQUENCE: 21

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Gly Gly Ser Met Gln Ile Phe Val Arg
    130                 135                 140

Thr Leu Thr Gly Arg Thr Ile Thr Leu Glu Val Glu Pro Ser Asp Thr
145                 150                 155                 160

Ile Glu Asn Val Arg Ala Arg Ile Gln Asp Arg Glu Gly Ile Pro Pro
                165                 170                 175

Asp Gln Gln Arg Leu Ile Phe Ala Gly Arg Gln Leu Glu Asp Gly Arg
            180                 185                 190

Thr Leu Ser Asp Tyr Asn Ile Gln Arg Glu Ser Thr Leu His Leu Val
        195                 200                 205

Leu Arg Leu Arg Gly Gly Gly Ser Ser Gln Ser Asn Arg Glu Leu Val
    210                 215                 220
```

-continued

Val Asp Phe Leu Ser Tyr Lys Leu Ser Gln Lys Gly Tyr Ser Trp Ser
225 230 235 240

Gln Phe Ser Asp Val Glu Glu Asn Arg Thr Glu Ala Pro Glu Gly Thr
245 250 255

Glu Ser Glu Met Glu Thr Pro Ser Ala Ile Asn Gly Asn Pro Ser Trp
260 265 270

His Leu Ala Asp Ser Pro Ala Val Asn Gly Ala Thr Gly His Ser Ser
275 280 285

Ser Leu Asp Ala Arg Glu Val Ile Pro Met Ala Ala Val Lys Gln Ala
290 295 300

Leu Arg Glu Ala Gly Asp Glu Phe Glu Leu Arg Tyr Arg Arg Ala Phe
305 310 315 320

Ser Asp Leu Thr Ser Gln Leu His Ile Thr Pro Gly Thr Ala Tyr Gln
325 330 335

Ser Phe Glu Gln Val Val Asn Glu Leu Phe Arg Asp Gly Val Asn Trp
340 345 350

Gly Arg Ile Val Ala Phe Phe Ser Phe Gly Gly Ala Leu Cys Val Glu
355 360 365

Ser Val Asp Lys Glu Met Gln Val Leu Val Ser Arg Ile Ala Ala Trp
370 375 380

Met Ala Thr Tyr Leu Asn Asp His Leu Glu Pro Trp Ile Gln Glu Asn
385 390 395 400

Gly Gly Trp Asp Thr Phe Val Glu Leu Tyr Gly Asn Asn Ala Ala Ala
405 410 415

Glu Ser Arg Lys Gly Gln Glu Arg Phe Asn Arg Trp Phe Leu Thr Gly
420 425 430

Met Thr Val Ala Gly Val Val Leu Leu Gly Ser Leu Phe Ser Arg Lys
435 440 445

<210> SEQ ID NO 22
<211> LENGTH: 369
<212> TYPE: PRT
<213> ORGANISM: Artificial Sequence
<220> FEATURE:
<223> OTHER INFORMATION: cpKFR4-BclxL

<400> SEQUENCE: 22

Met Asp Thr Thr Glu Lys Glu Thr Phe Cys Arg Ala Ala Thr Val Leu
1 5 10 15

Arg Gln Phe Tyr Ser His His Glu Lys Asp Thr Arg Cys Leu Gly Ala
20 25 30

Thr Ala Gln Gln Phe His Arg His Lys Gln Leu Ile Arg Phe Leu Lys
35 40 45

Arg Leu Asp Arg Asn Leu Trp Gly Leu Ala Gly Leu Asn Ser Cys Pro
50 55 60

Val Lys Glu Ala Asn Gln Ser Thr Leu Glu Asn Phe Leu Glu Arg Leu
65 70 75 80

Lys Thr Ile Met Lys Glu Lys Phe Arg Lys Cys Ser Ser Gly Gly Asn
85 90 95

Gly Gly His Lys Cys Asp Ile Thr Leu Gln Glu Ile Ile Lys Thr Leu
100 105 110

Asn Ser Leu Thr Glu Gln Lys Thr Leu Cys Thr Glu Leu Thr Val Thr
115 120 125

Asp Ile Phe Ala Ala Ser Lys Gly Ser Ser Gln Ser Asn Arg Glu Leu
130 135 140

Val Val Asp Phe Leu Ser Tyr Lys Leu Ser Gln Lys Gly Tyr Ser Trp
145 150 155 160

Ser Gln Phe Ser Asp Val Glu Glu Asn Arg Thr Glu Ala Pro Glu Gly
165 170 175

Thr Glu Ser Glu Met Glu Thr Pro Ser Ala Ile Asn Gly Asn Pro Ser
180 185 190

Trp His Leu Ala Asp Ser Pro Ala Val Asn Gly Ala Thr Gly His Ser
195 200 205

Ser Ser Leu Asp Ala Arg Glu Val Ile Pro Met Ala Ala Val Lys Gln
210 215 220

Ala Leu Arg Glu Ala Gly Asp Glu Phe Glu Leu Arg Tyr Arg Arg Ala
225 230 235 240

Phe Ser Asp Leu Thr Ser Gln Leu His Ile Thr Pro Gly Thr Ala Tyr
245 250 255

Gln Ser Phe Glu Gln Val Val Asn Glu Leu Phe Arg Asp Gly Val Asn
260 265 270

Trp Gly Arg Ile Val Ala Phe Phe Ser Phe Gly Gly Ala Leu Cys Val
275 280 285

Glu Ser Val Asp Lys Glu Met Gln Val Leu Val Ser Arg Ile Ala Ala
290 295 300

Trp Met Ala Thr Tyr Leu Asn Asp His Leu Glu Pro Trp Ile Gln Glu
305 310 315 320

Asn Gly Gly Trp Asp Thr Phe Val Glu Leu Tyr Gly Asn Asn Ala Ala
325 330 335

Ala Glu Ser Arg Lys Gly Gln Glu Arg Phe Asn Arg Trp Phe Leu Thr
340 345 350

Gly Met Thr Val Ala Gly Val Val Leu Leu Gly Ser Leu Phe Ser Arg
355 360 365

Lys

<210> SEQ ID NO 23
<211> LENGTH: 449
<212> TYPE: PRT
<213> ORGANISM: Artificial Sequence
<220> FEATURE:
<223> OTHER INFORMATION: cpS4-Ub-BclxL

<400> SEQUENCE: 23

Met Asp Thr Thr Glu Lys Glu Thr Phe Cys Arg Ala Ala Thr Val Leu
1 5 10 15

Arg Gln Phe Tyr Ser His His Glu Lys Asp Thr Arg Cys Leu Gly Ala
20 25 30

Thr Ala Gln Gln Phe His Arg His Lys Gln Leu Ile Arg Phe Leu Lys
35 40 45

Arg Leu Asp Arg Asn Leu Trp Gly Leu Ala Gly Leu Asn Ser Cys Pro
50 55 60

Val Lys Glu Ala Asn Gln Ser Thr Leu Glu Asn Phe Leu Glu Arg Leu
65 70 75 80

Arg Val Ile Met Gln Ser Lys Trp Phe Lys Cys Gly Ala Gly Gly Asn
85 90 95

Gly Gly His Lys Cys Asp Ile Thr Leu Gln Glu Ile Ile Lys Thr Leu
100 105 110

Asn Ser Leu Thr Glu Gln Lys Thr Leu Cys Thr Glu Leu Thr Val Thr
115 120 125

Asp Ile Phe Ala Ala Ser Lys Gly Gly Gly Ser Met Gln Ile Phe Val 130 135 140

Arg Thr Leu Thr Gly Arg Thr Ile Thr Leu Glu Val Glu Pro Ser Asp
145 150 155 160

Thr Ile Glu Asn Val Arg Ala Arg Ile Gln Asp Arg Glu Gly Ile Pro
165 170 175

Pro Asp Gln Gln Arg Leu Ile Phe Ala Gly Arg Gln Leu Glu Asp Gly
180 185 190

Arg Thr Leu Ser Asp Tyr Asn Ile Gln Arg Glu Ser Thr Leu His Leu
195 200 205

Val Leu Arg Leu Arg Gly Gly Gly Ser Ser Gln Ser Asn Arg Glu Leu
210 215 220

Val Val Asp Phe Leu Ser Tyr Lys Leu Ser Gln Lys Gly Tyr Ser Trp
225 230 235 240

Ser Gln Phe Ser Asp Val Glu Glu Asn Arg Thr Glu Ala Pro Glu Gly
245 250 255

Thr Glu Ser Glu Met Glu Thr Pro Ser Ala Ile Asn Gly Asn Pro Ser
260 265 270

Trp His Leu Ala Asp Ser Pro Ala Val Asn Gly Ala Thr Gly His Ser
275 280 285

Ser Ser Leu Asp Ala Arg Glu Val Ile Pro Met Ala Ala Val Lys Gln
290 295 300

Ala Leu Arg Glu Ala Gly Asp Glu Phe Glu Leu Arg Tyr Arg Arg Ala
305 310 315 320

Phe Ser Asp Leu Thr Ser Gln Leu His Ile Thr Pro Gly Thr Ala Tyr
325 330 335

Gln Ser Phe Glu Gln Val Val Asn Glu Leu Phe Arg Asp Gly Val Asn
340 345 350

Trp Gly Arg Ile Val Ala Phe Phe Ser Phe Gly Gly Ala Leu Cys Val
355 360 365

Glu Ser Val Asp Lys Glu Met Gln Val Leu Val Ser Arg Ile Ala Ala
370 375 380

Trp Met Ala Thr Tyr Leu Asn Asp His Leu Glu Pro Trp Ile Gln Glu
385 390 395 400

Asn Gly Gly Trp Asp Thr Phe Val Glu Leu Tyr Gly Asn Asn Ala Ala
405 410 415

Ala Glu Ser Arg Lys Gly Gln Glu Arg Phe Asn Arg Trp Phe Leu Thr
420 425 430

Gly Met Thr Val Ala Gly Val Val Leu Leu Gly Ser Leu Phe Ser Arg
435 440 445

Lys

<210> SEQ ID NO 24
<211> LENGTH: 369
<212> TYPE: PRT
<213> ORGANISM: Artificial Sequence
<220> FEATURE:
<223> OTHER INFORMATION: cpS4-BclxL

<400> SEQUENCE: 24

Met Asp Thr Thr Glu Lys Glu Thr Phe Cys Arg Ala Ala Thr Val Leu
1 5 10 15

Arg Gln Phe Tyr Ser His His Glu Lys Asp Thr Arg Cys Leu Gly Ala
20 25 30

Thr Ala Gln Gln Phe His Arg His Lys Gln Leu Ile Arg Phe Leu Lys
35 40 45

-continued

```
Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Lys Gly Ser Ser Gln Ser Asn Arg Glu Leu
    130                 135                 140

Val Val Asp Phe Leu Ser Tyr Lys Leu Ser Gln Lys Gly Tyr Ser Trp
145                 150                 155                 160

Ser Gln Phe Ser Asp Val Glu Glu Asn Arg Thr Glu Ala Pro Glu Gly
                165                 170                 175

Thr Glu Ser Glu Met Glu Thr Pro Ser Ala Ile Asn Gly Asn Pro Ser
            180                 185                 190

Trp His Leu Ala Asp Ser Pro Ala Val Asn Gly Ala Thr Gly His Ser
        195                 200                 205

Ser Ser Leu Asp Ala Arg Glu Val Ile Pro Met Ala Ala Val Lys Gln
    210                 215                 220

Ala Leu Arg Glu Ala Gly Asp Glu Phe Glu Leu Arg Tyr Arg Arg Ala
225                 230                 235                 240

Phe Ser Asp Leu Thr Ser Gln Leu His Ile Thr Pro Gly Thr Ala Tyr
                245                 250                 255

Gln Ser Phe Glu Gln Val Val Asn Glu Leu Phe Arg Asp Gly Val Asn
            260                 265                 270

Trp Gly Arg Ile Val Ala Phe Phe Ser Phe Gly Gly Ala Leu Cys Val
        275                 280                 285

Glu Ser Val Asp Lys Glu Met Gln Val Leu Val Ser Arg Ile Ala Ala
    290                 295                 300

Trp Met Ala Thr Tyr Leu Asn Asp His Leu Glu Pro Trp Ile Gln Glu
305                 310                 315                 320

Asn Gly Gly Trp Asp Thr Phe Val Glu Leu Tyr Gly Asn Asn Ala Ala
                325                 330                 335

Ala Glu Ser Arg Lys Gly Gln Glu Arg Phe Asn Arg Trp Phe Leu Thr
            340                 345                 350

Gly Met Thr Val Ala Gly Val Val Leu Leu Gly Ser Leu Phe Ser Arg
        355                 360                 365

Lys
```

<210> SEQ ID NO 25
<211> LENGTH: 390
<212> TYPE: DNA
<213> ORGANISM: Artificial Sequence
<220> FEATURE:
<223> OTHER INFORMATION: IL-4

<400> SEQUENCE: 25

```
atgcacaaat gcgacattac cctgcaagag atcattaaga ccctgaacag cctgaccgag      60

caaaagaccc tgtgtaccga actgaccgtc acggacatct tcgctgcgtc caaggacact     120

acggaaaagg aaacgttctg tcgtgcggcg acggtgctgc gccagttcta cagccaccat     180
```

-continued

```
gagaaagata cccgttgcct cggtgcgacc gcgcaacagt tccaccgtca caaacagctg    240

attcgcttcc tgaagcgtct ggatcgcaac ctgtggggtt tggcgggtct gaactcctgt    300

ccagtcaaag aagccaatca gtctacgctg gaaaactttt tggagcgtct gaaaactatc    360

atgcgtgaga agtacagcaa atgcagcagc                                     390


<210> SEQ ID NO 26
<211> LENGTH: 402
<212> TYPE: DNA
<213> ORGANISM: Artificial Sequence
<220> FEATURE:
<223> OTHER INFORMATION: cpIL4

<400> SEQUENCE: 26

atggatacca ccgagaaaga aacgttctgc cgtgctgcca ctgtcctgcg ccagttttac     60

agccatcacg aaaaggacac ccgttgcctg ggtgcgacgg cgcagcaatt ccaccgccac    120

aaacagctga ttcgtttcct gaagcgtctg gaccgtaacc tgtggggtct ggcgggtctg    180

aacagctgtc cagtgaaaga agcgaatcag agcaccttgg agaatttcct cgaacgcctg    240

aaaaccatca tgcgtgagaa atacagcaag tgttctagcg gcggtaacgg tggccacaaa    300

tgcgatatca ccctgcaaga gatcattaag acgctgaact ccttgacgga acaaaagacc    360

ctgtgtactg agctgacggt caccgacatt ttcgcggcgt cc                       402


<210> SEQ ID NO 27
<211> LENGTH: 402
<212> TYPE: DNA
<213> ORGANISM: Artificial Sequence
<220> FEATURE:
<223> OTHER INFORMATION: cpKFR

<400> SEQUENCE: 27

atggatacta ccgagaaaga aacgttttgc cgtgctgcga ccgtcctgcg tcagttctac     60

agccaccacg aaaaggacac ccgctgtctg ggtgcgactg cccaacaatt ccatcgtcac    120

aaacagctga ttcgtttcct gaagcgtctg gaccgcaacc tgtggggtct ggcgggcttg    180

aactcctgcc cagtcaaaga agcgaaccaa agcaccctgg aaaacttctt ggagcgtctg    240

aaaacgatca tgaaagagaa gttccgcaag tgtagcagcg gtggtaatgg tggccacaag    300

tgcgacatta cgctgcagga aatcattaag accctgaact ctctgaccga gcagaaaacc    360

ctctgtaccg agctgacggt gacggatatc tttgcggcga gc                       402


<210> SEQ ID NO 28
<211> LENGTH: 402
<212> TYPE: DNA
<213> ORGANISM: Artificial Sequence
<220> FEATURE:
<223> OTHER INFORMATION: cpS4

<400> SEQUENCE: 28

atggatacca ccgaaaaaga aactttttgt cgtgccgcga ctgtcctgcg ccagttctac     60

agccaccacg aaaaggacac ccgttgcctg ggtgcgaccg ctcaacaatt ccatcgccac    120

aaacagctga ttcgtttcct gaaacgtctg gatcgcaacc tgtggggtct ggcgggtttg    180

aacagctgtc cagtcaaaga agcgaaccag agcaccctgg aaaactttct ggagcgtctg    240

cgtgttatca tgcagagcaa gtggttcaag tgcggtgcgg gtggcaatgg tggccacaag    300

tgtgacatta ccttgcaaga gattatcaaa acgctgaact ctctgaccga gcaaaagacg    360

ctgtgcaccg agctgacggt gacggacatc ttcgcggcgt cc                       402
```

<210> SEQ ID NO 29
<211> LENGTH: 696
<212> TYPE: DNA
<213> ORGANISM: Artificial Sequence
<220> FEATURE:
<223> OTHER INFORMATION: variant BclxL

<400> SEQUENCE: 29

```
tctcagtcta accgcgaact ggtggtggac ttcctgtctt ataaactgag ccagaaaggc     60

tactcctgga gccagttcag cgacgtagag gagaaccgta ccgaagctcc tgaaggcacc    120

gagagcgaga tggaaacccc atccgcgatt aacggcaacc cgtcctggca cctggctgat    180

tctccggcgg taaacggcgc aactggtcat tctagctccc tggatgcacg tgaagtaatc    240

ccgatggccg cggttaaaca ggcgctgcgt gaagctggtg acgaatttga gctgcgctac    300

cgccgtgcat tttctgatct gacctcccag ctgcacatca cgccgggtac cgcataccaa    360

agcttcgaac aggtggttaa cgaactgttt cgtgacggcg tcaactgggg ccgcatcgtg    420

gcctttttct ctttcggcgg tgccctgtgc gtcgaatctg ttgacaaaga aatgcaggtt    480

ctggtgagcc gtattgcggc ttggatggca acttatctga acgatcacct ggaaccgtgg    540

atccaggaaa acggtggttg ggataccttc gttgaactgt acggtaacaa tgctgcggcg    600

gaatcccgta agggtcaaga acgtttcaat cgctggttcc tgaccggcat gactgttgct    660

ggtgtagttc tgctgggttc tctgttctcc cgtaaa                              696
```

<210> SEQ ID NO 30
<211> LENGTH: 1119
<212> TYPE: DNA
<213> ORGANISM: Artificial Sequence
<220> FEATURE:
<223> OTHER INFORMATION: cpIL4-BclxL

<400> SEQUENCE: 30

```
atggacacga ctgagaaaga gaccttctgc cgtgcagcaa ctgttctgcg tcagttctat     60

tcccaccacg aaaaagatac gcgttgcctg ggtgctactg cgcagcagtt ccatcgtcat    120

aagcaactga ttcgctttct gaaacgtctg gaccgtaacc tgtggggtct ggccggtctg    180

aacagctgcc cggtcaaaga agcgaaccag tccactctgg aaaacttcct ggaacgcctg    240

aagaccatca tgcgcgaaaa atactccaag tgttccagcg gcggcaacgg cggtcacaaa    300

tgtgacatca ccctgcagga aatcatcaaa actctgaatt ctctgactga gcagaaaacc    360

ctgtgtaccg aactgaccgt gaccgatatt tttgccgctt ctaaagcgtc tggtggcccg    420

gaatctcagt ctaaccgcga actggtggtg gacttcctgt cttataaact gagccagaaa    480

ggctactcct ggagccagtt cagcgacgta gaggagaacc gtaccgaagc tcctgaaggc    540

accgagagcg agatggaaac cccatccgcg attaacggca acccgtcctg gcacctggct    600

gattctccgg cggtaaacgg cgcaactggt cattctagct ccctggatgc acgtgaagta    660

atcccgatgg ccgcggttaa acaggcgctg cgtgaagctg gtgacgaatt tgagctgcgc    720

taccgccgtg cattttctga tctgacctcc cagctgcaca tcacgccggg taccgcatac    780

caaagcttcg aacaggtggt taacgaactg tttcgtgacg gcgtcaactg gggccgcatc    840

gtggcctttt tctctttcgg cggtgccctg tgcgtcgaat ctgttgacaa agaaatgcag    900

gttctggtga gccgtattgc ggcttggatg gcaacttatc tgaacgatca cctggaaccg    960

tggatccagg aaaacggtgg ttgggatacc ttcgttgaac tgtacggtaa caatgctgcg   1020
```

-continued

```
gcggaatccc gtaagggtca agaacgtttc aatcgctggt tcctgaccgg catgactgtt   1080

gctggtgtag ttctgctggg ttctctgttc tcccgtaaa                          1119


<210> SEQ ID NO 31
<211> LENGTH: 1347
<212> TYPE: DNA
<213> ORGANISM: Artificial Sequence
<220> FEATURE:
<223> OTHER INFORMATION: cpIL4-Ub-BclxL

<400> SEQUENCE: 31

atggacacga ctgagaaaga gaccttctgc cgtgcagcaa ctgttctgcg tcagttctat     60

tcccaccacg aaaaagatac gcgttgcctg ggtgctactg cgcagcagtt ccatcgtcat    120

aagcaactga ttcgctttct gaaacgtctg gaccgtaacc tgtggggtct ggccggtctg    180

aacagctgcc cggtcaaaga agcgaaccag tccactctgg aaaacttcct ggaacgcctg    240

aagaccatca tgcgcgaaaa atactccaag tgttccagcg gcggcaacgg cggtcacaaa    300

tgtgacatca ccctgcagga aatcatcaaa actctgaatt ctctgactga gcagaaaacc    360

ctgtgtaccg aactgaccgt gaccgatatt tttgccgctt ctaaaggtgg cggctctatg    420

caaattttcg ttcgtaccct gacgggtcgt accatcactc tggaagtaga accgagcgac    480

acgatcgaaa atgtccgcgc acgcatccaa gaccgcgaag gcattccacc ggatcagcag    540

cgtctgatct tcgccggtcg ccagctggag gatggtcgta ctctgtccga ttataacatc    600

cagcgtgaat ccaccctgca cctggtgctg cgtctgcgtg gcggtggtag ctctcagtct    660

aaccgcgaac tggtggtgga cttcctgtct tataaactga gccagaaagg ctactcctgg    720

agccagttca gcgacgtaga ggagaaccgt accgaagctc ctgaaggcac cgagagcgag    780

atggaaaccc catccgcgat taacggcaac ccgtcctggc acctggctga ttctccggcg    840

gtaaacggcg caactggtca ttctagctcc ctggatgcac gtgaagtaat cccgatggcc    900

gcggttaaac aggcgctgcg tgaagctggt gacgaatttg agctgcgcta ccgccgtgca    960

ttttctgatc tgacctccca gctgcacatc acgccgggta ccgcatacca aagcttcgaa   1020

caggtggtta acgaactgtt tcgtgacggc gtcaactggg gccgcatcgt ggccttttc   1080

tctttcggcg gtgccctgtg cgtcgaatct gttgacaaag aaatgcaggt tctggtgagc   1140

cgtattgcgg cttggatggc aacttatctg aacgatcacc tggaaccgtg gatccaggaa   1200

aacggtggtt gggatacctt cgttgaactg tacggtaaca atgctgcggc ggaatcccgt   1260

aagggtcaag aacgtttcaa tcgctggttc ctgaccggca tgactgttgc tggtgtagtt   1320

ctgctgggtt ctctgttctc ccgtaaa                                       1347
```

INTERLEUKIN-4 RECEPTOR-BINDING FUSION PROTEINS AND USES THEREOF

CROSS-REFERENCE TO RELATED APPLICATIONS

This application is the U.S. National Phase of International Application No. PCT/CA2014/050916, filed Sep. 24, 2014, which claims the benefit of U.S. Provisional Application No. 61/881,930, filed Sep. 24, 2013, the references of which are hereby incorporated by reference in their entirety.

FIELD OF INVENTION

The present invention relates to interleukin-4 receptor-binding protein fusions. More specifically, the invention provides, in part, fusion proteins that include an interleukin-4 or interleukin-13 protein moiety joined to an anti-apoptotic Bcl-2 family member protein moiety.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Apr. 26, 2018, entitled 117802_5003_US_Updated_Sequence.txt which is 52 kilobytes in size.

BACKGROUND OF THE INVENTION

Interleukin-4 (IL-4) is a pleiotropic cytokine produced by activated T cells, and is the ligand for the IL-4 receptor (IL-4R), which can also bind to interleukin-13 (IL-13). IL-4, like many cytokines, first binds to a high-affinity receptor chain (designated "α"), followed by binding of the IL-4-α chain complex with a second low-affinity receptor chain designated "γc". Therefore, the primary binding chain for IL-4 is the IL-4 receptor alpha (IL-4Rα), which binds with high affinity ($K_D$=~$10^{-10}$ M). The IL-4/IL-4Rα complex can then bind the second component of the IL-4 receptor, γc (the "Type I" receptor) with relatively low affinity. Additionally, the IL-4/IL-4Rα complex can also bind the interleukin-13 (IL-13) receptor α1 (IL-13R α1) (the "Type II" receptor).

Different cell types express different amounts of the Type I and Type II receptor chains. For example, while IL-4Rα is present on most cells, γc is generally expressed on hematopoietic cells and IL-13R α1 is generally expressed on non-hematopoietic cells. Accordingly, γc, but not IL-13R α1, is found on T cells, natural killer (NK) cells, basophils, mast cells, and most mouse B cells (most human B cells express both γc and IL-13R α1).

Some bone marrow-derived cells, including macrophages and dendritic cells, express both γc and IL-13R α1 and consequently respond to both IL-4 and IL-13. IL-13R α1, but little or no γc, is found on most non-bone marrow-derived cells, including smooth muscle and epithelial cells.

Variant IL-4 molecules having differential selectivities for Type I and Type II receptors have been proposed (Junttila et al. Nature Chemical Biology 8:990-998, 2012.)

Circularly permuted molecules are those in which the termini of a linear molecule (e.g., ligand) have been joined together, either directly or via a linker, to produce a circular molecule, after which the circular molecule is opened at another location to produce a new linear molecule with termini different from the termini of the original molecule.

Circularly permuted variants of IL-4 have been described in, for example, U.S. Pat. No. 6,011,002, issued Jan. 4, 2000, to Pastan et al.

Programmed cell death or "apoptosis," is a common phenomenon in the development of animal cells and is both positively and negatively regulated. In addition to its involvement in neuronal and lymphoid system development and overall cell population homeostasis, apoptosis also plays a significant role in various diseases and injuries resulting from aberrant regulation of apoptotic pathways. For example, aberrant activation of neuronal cell death by apoptosis has been implicated in many neurodegenerative diseases and conditions, such as Alzheimer disease (Barinaga, Science 281:1303-1304), Huntington's disease, spinal-muscular atrophy, neuronal damage caused during stroke (reviewed in Rubin, British Med. Bulle., 53(3):617-631, 1997; and Barinaga, Science 281:1302-1303), transient ischemic neuronal injury (e.g., spinal cord injury), etc. Conversely, aberrant suppression of apoptosis can result in hyperproliferation of cells, leading to cancer and other hyperproliferative disorders.

Apoptosis is regulated by a number of proteins, including members of the Bcl-2 family. Bcl-2 was one of the first proteins identified as regulating apoptosis (Cleary et al., Cell 47:19-28, 1986; Tsujimoto and Croce, Proc. Natl. Acad. Sci. USA 83:5214-5218, 1986). Since its discovery, several Bcl-2-related proteins ("Bcl-2 family proteins" or "Bcl-2 family members") have been identified as regulators of apoptosis (White, Genes Dev. 10:1-15, 1996; Yang et al., Cell 80:285-291, 1995).

Several therapeutic agents for treatment of neurodegenerative diseases, cancer, etc. have been explored but exhibit limitations that restrict their use in the clinic. For example, many chemotherapeutic agents act by inducing apoptosis in proliferating neoplastic cells, but their therapeutic value is limited by the extent to which they are toxic to normal cells. Treatment with standard apoptosis inhibitory molecules, for instance peptide-type caspase inhibitors (e.g., DEVD-type), has proven unsatisfactory for clinical work due to low membrane permeability of these inhibitors.

Targeted immunotoxins (genetic or biochemical fusions between a toxic molecule, for instance a bacterial toxin, and a targeting domain derived, typically from an antibody molecule) have been proposed in attempts to selectively eliminate cancer cells. For example, diphtheria toxin (DT) variants have been generated and tested for their ability to selectively kill cancer cells (Thorpe et al., Nature 271:752-755, 1978; Laske et al., Nature Medicine 3:1362-1368, 1997). Similarly, *Pseudomonas* exotoxin (PE) fusion proteins have been investigated as potential cancer therapeutics (Kreitman and Pastan, Blood 90:252-259, 1997; Shimamura et al. Cancer Res. 67:9903-9912; 2007). DT-BclxL fusion proteins have been tested for their ability to block apoptosis induced by staurosporin, γ-irradiation, and poliovirus in a variety of cells types (Youle et al., Proc Natl Acad Sci. 96:9563-9567). Granulocyte-macrophage colony-stimulating factor BclxL (GM-CSF-BclxL) fusion proteins have been shown to increase the proliferation of human monocytes, and protect cells from induced cell death (Youle et al., JBC 282(15):11246-11254).

SUMMARY OF THE INVENTION

The present invention relates to interleukin-4 fusion proteins. More specifically, the invention provides, in part, fusion proteins that include an interleukin-4 receptor-binding protein moiety, such as an interleukin-4 or interleukin-13, joined to an anti-apoptotic Bcl-2 family member protein moiety and uses thereof.

In one aspect, the invention provides a fusion protein including an interleukin-4 (IL-4) receptor binding protein and a Bcl-2 family polypeptide.

In some embodiments, the IL-4 receptor binding protein may be circularly permuted (cp).

In some embodiments, the Bcl-2 family polypeptide may be an anti-apoptotic Bcl-2 family polypeptide (such as Bcl-$x_L$, Bcl-w or Bcl-2). The fusion protein may be capable of enhancing cell survival, inhibiting cell death or apoptosis, protecting against cell death, increasing cell activation or promoting cell maturation of a target cell expressing an IL-4R.

In some embodiments, the IL-4 receptor binding protein may be a mutant IL-4 or IL-13 selective for binding to a Type I or a Type II IL-4 receptor (IL-4R). The mutant IL-4 selective for binding to a Type II IL-4R may include a KFR variant or a KF variant. The mutant IL-4 selective for binding to a Type I IL-4R may include an RGA variant. The mutant IL-13 may be an A11 variant or a DN variant.

In some embodiments, the fusion protein may further include a linker. The linker may have the sequence GS or may be a ubiquitin or ubiquitin variant molecule.

In some aspects, there is provided a nucleic acid molecule encoding a fusion protein as described herein, or a vector including the nucleic acid molecule, or a host cell including the vector.

In some aspects, there is provided a pharmaceutical composition including a fusion protein as described herein, a nucleic acid molecule encoding the fusion protein, or a vector including the nucleic acid molecule, or a host cell including the vector.

In some aspects, there is provided a method of stimulating cell proliferation, enhancing cell survival, inhibiting cell death or apoptosis, protecting against cell death, increasing cell activation or promoting cell maturation by administering a fusion protein including an anti-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of stimulating cell proliferation, enhancing cell survival, inhibiting cell death or apoptosis, protecting against cell death, increasing cell activation or promoting cell maturation by contacting a target cell that expresses an IL-4R with a fusion protein including an anti-apoptotic Bcl-2 family polypeptide, a nucleic acid molecule encoding the fusion protein, or a vector including the nucleic acid molecule.

In some aspects, there is provided a method of enhancing an immune response by administering a fusion protein including an anti-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of enhancing an immune response by contacting a target cell that expresses an IL-4R with a fusion protein including an anti-apoptotic Bcl-2 family polypeptide, a nucleic acid molecule encoding the fusion protein, or a vector including the nucleic acid molecule.

In some aspects, there is provided a method of treating a neurological disorder or condition or an autoimmune disorder by administering a fusion protein including an anti-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of treating a neurological disorder or condition by contacting a neuronal cell or stem cell that expresses an IL-4R with a fusion protein including an anti-apoptotic Bcl-2 family polypeptide, a nucleic acid molecule encoding the fusion protein, or a vector including the nucleic acid molecule.

In some aspects, there is provided a composition including a fusion protein including an anti-apoptotic Bcl-2 family polypeptide and further including a GM-CSF-Bcl-$X_L$ fusion protein.

In some aspects, there is provided a method of stimulating cell proliferation by further administering a GM-CSF-Bcl-$X_L$ fusion protein or contacting a cell with a GM-CSF-Bcl-$X_L$ fusion protein.

In some aspects, there is provided a use of a fusion protein including an anti-apoptotic Bcl-2 family polypeptide, a nucleic acid molecule encoding the fusion protein, or a vector including the nucleic acid molecule, for stimulating cell proliferation, enhancing an immune response or treating a neurological disorder or an autoimmune disorder in a subject in need thereof.

In various embodiments of the alternative aspects, the subject may be a human.

In some aspects, there is provided a method of propagating or expanding engineered T cells for use in adoptive cell transfer therapy or chimeric antigen receptor (CAR) therapy by contacting the engineered T cell with the fusion protein including an anti-apoptotic Bcl-2 family polypeptide, a nucleic acid molecule encoding the fusion protein, or a vector including the nucleic acid molecule.

This summary does not necessarily describe all features of the invention.

BRIEF DESCRIPTION OF THE DRAWINGS

These and other features of the invention will become more apparent from the following description in which reference is made to the appended drawings wherein:

FIGS. 4A-D show the nucleic acid (SEQ ID NOs: 30 and 31) and amino sequences (SEQ ID NOs: 18 and 20) of cpIL4-BclxL (A-B) and cpIL4-Ub-BclxL (C-D) fusion constructs.

DETAILED DESCRIPTION

Figure 1A:
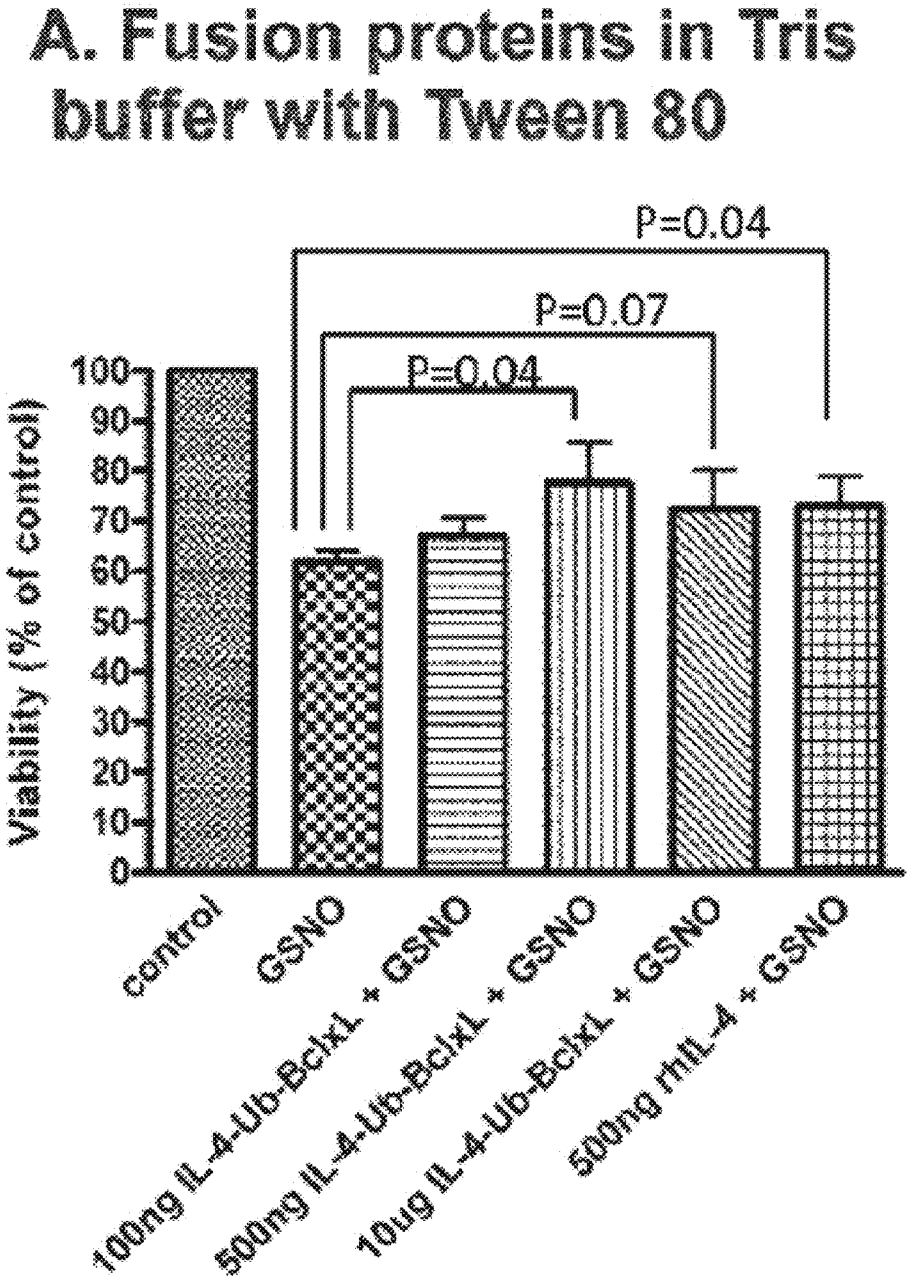
FIG. 1 is a graph showing the effect of cpIL-4-Ub-BclxL or rhIL-4 on neural cell (SH-SY5Y) survival after insult with GSNO.

The present disclosure provides, in part, a fusion protein including an IL-4R binding protein joined to an anti-apoptotic Bcl-2 family protein and uses thereof.

IL-4R Binding Proteins

IL-4R binding proteins include IL-4 and IL-13.

IL-4 proteins or IL-4 "protein moieties" include native IL-4 proteins, as well as variant IL-4 proteins. A "native" or "wild type" IL-4 sequence, as used herein, refers to a human IL-4 sequence, whether purified from natural sources or made using recombinant techniques, and including the amino acid sequence (with an additional methionine at the N-terminus) as follows:

(SEQ ID NO: 1)

MHKCDITLQEIIKTLNSLTEQKTLCTELTVTDIFAASKNTTEKETF

CRAATVLRQFYSHHEKDTRCLGATAQQFHRHKQLIRFLKRLD

RNLWGLAGLNSCPVKEANQSTLENFLERLKTIMREKYSKCSS.

Alternative human IL-4 sequences include the amino acid sequence (with an additional methionine at the N-terminus) as follows:

(SEQ ID NO: 2)

MHKCDITLQEIIKTLNSLTEQKTLCTELTVTDIFAASKDTTEKETFCR

AATVLRQFYSHHEKDTRCLGATAQQFHRHKQLIRFLKRLDRNLWGLAGL

NSCPVKEANQSTLENFLERLKTIMREKYSKCSS.

In some embodiments, IL-4 proteins that can be used in the fusion proteins of the present disclosure are variant IL-4 proteins that have increased selectivity for γc (Type I receptor) relative to IL-13R α1 (Type II receptor) or vice versa as described, for example, in Junttila et al. (Nature Chemical Biology 8:990-998, 2012). In some embodiments, a variant IL-4 protein that has increased selectivity for γc (Type I receptor) is an IL-4 protein that includes the following mutations relative to the sequence of native human IL-4 (e.g., SEQ ID NO: 1) or an alternative IL-4 sequence (e.g., SEQ ID NO:2), the numbering excluding the methionine at the N-terminus: R121Q/Y124W/S125F (the "RGA" or "super-4" or "S4" variant) as described, for example, in Junttila et al. (Nature Chemical Biology 8:990-998, 2012).

In some embodiments, a variant IL-4 protein that has increased selectivity for IL-13R α1 (Type II receptor) is an IL-4 protein that includes the following mutations relative to the sequence of native human IL-4 (e.g., SEQ ID NO: 1) or an alternative IL-4 sequence (e.g., SEQ ID NO:2), the numbering excluding the methionine at the N-terminus: R121K/Y124F/S125R (the "KFR" or "KFR4" variant) or R121K/Y124F (the "KF" variant).

In some embodiments, IL-4 proteins that can be used in the fusion proteins of the present disclosure are circularly permuted (cp), as described in, for example, U.S. Pat. No. 6,011,002, issued Jan. 4, 2000, to Pastan et al. In some embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus are joined to residues 1-37 with a GGNGG (SEQ ID NO: 32) linker and an initial methionine residue, as follows:

(SEQ ID NO: 3)

MDTTEKETFCRAATVLRQFYSHHEKDTRCLGATAQQFHRHKQLIRFLKR

LDRNLWGLAGLN SCPVKEANQSTLEN FLERLKTI M REKYSKCSS

GGNGGH KCDITLQEI IKTLNSLTEQKTLCTE LTVTDIFAAS.

In alternative embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus are joined to residues 1-37 with a GGNGG (SEQ ID NO: 32) linker and an initial methionine residue, in the context of the "RGA" or "super-4" or "S4" variant, as follows:

(SEQ ID NO: 4)

MDTTEKETFCRAATVLRQFYSHHEKDTRCLGATAQQFHRHKQLIRFLKRL

DRNLWGLAGLN SCPVKEANQSTLENFLERLRVIMQ§KWFKCGAGGNGGH

KCDITLQEII KTLNSL TEQKTLCT ELTVTDIFAAS.

In alternative embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus are joined to residues 1-37 with a GGNGG (SEQ ID NO: 32) linker and an initial methionine residue, in the context of a "KFR" variant, as follows:

(SEQ ID NO: 5)

MDTTEKETFCRAATVLRQFYSHHEKDTRCLGATAQQFHRHKQLIRFLKR

LDRNLWGLAGLN SCPVKEANQSTLEN FLERLKTI MKEKFRKC-
SSGGNGG

H KCDITLQEI IKTLNSLTEQKTLCTE LTVTDIFAAS.

In alternative embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus are joined to residues 1-37 with a GGNGG (SEQ ID NO: 32) linker and an initial methionine residue, in the context of a "KF" variant, as follows:

(SEQ ID NO: 6)

MDTTEKETFCRAATVLRQFYSHHEKDTRCLGATAQQFHRHKQLIRFLKRL

DRNLWGLAGLN SCPVKEANQSTLEN FLERLKTI MKEKfKCSSGGNGG

H KCDITLQEIIKTLNSL TEQKTLCTEL TVTDIFAAS.

In alternative embodiments, a cpIL-4 protein that can be used in the fusion proteins of the present disclosure includes an IL-4 protein in which residues I 05-129 of native human IL-4 (e.g., SEQ ID NO: 1) or an alternative IL-4 sequence (e.g., SEQ ID NO:2), the numbering excluding the methionine at the N-terminus are joined to residues 1-104 with a GGNGG (SEQ ID NO: 32) linker and an initial methionine residue, as described in, for example, U.S. Pat. No. 6,011,002, issued Jan. 4, 2000, to Pastan et al.

Exemplary IL-4 proteins that can be used in the fusion proteins of the present disclosure include those described herein, as well as sequences having at least 80% sequence identity, at least 85%, at least 90%, at least 95%, at least 98% or even at least 99% sequence identity to native IL-4 ("variant IL-4 proteins"), as long as the variant IL-4 protein retains the ability to bind the IL-4 receptor, or retains increased selectivity for the γc (Type I receptor) relative to IL-13R α1 (Type II receptor) or vice versa as described, for example, in Junttila et al. (Nature Chemical Biology 8:990-998, 2012), or retains a desired biological activity.

It is to be understood that IL-4 proteins according to the present disclosure include fragments that can be smaller than the native 129 amino acid IL-4 protein, as long as the IL-4 protein fragment retains the ability to bind the IL-4 receptor, or retains increased selectivity for the γc (Type I receptor) relative to IL-13R α1 (Type II receptor) or vice versa as described, for example, in Junttila et al. (Nature Chemical Biology 8:990-998, 2012), or retains a desired biological activity, whether as a fragment of the native sequence, or in a cp form or fragment thereof.

It is also to be understood that the present disclosure encompasses nucleic acid molecules that encode an IL-4 protein as described herein or known in the art, including but not limited to RNA sequences corresponding to the DNA sequences described herein.

Exemplary IL-4 nucleic acid molecules include:

(IL4; SEQ ID NO: 25)
ATGCACAAATGCGACATTACCCTGCAAGAGATCATTAAGACCCTGAACAG

CCTGACCGAGCAAAAGACCCTGTGTACCGAACTGACCGTCACGGACATCT

TCGCTGCGTCCAAGGACACTACGGAAAAGGAAACGTTCTGTCGTGCGGCG

ACGGTGCTGCGCCAGTTCTACAGCCACCATGAGAAAGATACCCGTTGCCT

CGGTGCGACCGCGCAACAGTTCCACCGTCACAAACAGCTGATTCGCTTCC

TGAAGCGTCTGGATCGCAACCTGTGGGGTTTGGCGGGTCTGAACTCCTGT

CCAGTCAAAGAAGCCAATCAGTCTACGCTGGAAAACTTTTTGGAGCGTCT

GAAAACTATCATGCGTGAGAAGTACAGCAAATGCAGCAGC;

(cpIL4; SEQ ID NO: 26)
ATGGATACCACCGAGAAAGAAACGTTCTGCCGTGCTGCCACTGTCCTGCG

CCAGTTTTACAGCCATCACGAAAAGGACACCCGTTGCCTGGGTGCGACGG

CGCAGCAATTCCACCGCCACAAACAGCTGATTCGTTTCCTGAAGCGTCTG

GACCGTAACCTGTGGGGTCTGGCGGGTCTGAACAGCTGTCCAGTGAAAGA

AGCGAATCAGAGCACCTTGGAGAATTTCCTCGAACGCCTGAAAACCATCA

TGCGTGAGAAATACAGCAAGTGTTCTAGCGGCGGTAACGGTGGCCACAAA

TGCGATATCACCCTGCAAGAGATCATTAAGACGCTGAACTCCTTGACGGA

ACAAAAGACCCTGTGTACTGAGCTGACGGTCACCGACATTTTCGCGGCGT

CC;

(cpKFR; SEQ ID NO: 27)
ATGGATACTACCGAGAAAGAAACGTTTTGCCGTGCTGCGACCGTCCTGCG

TCAGTTCTACAGCCACCACGAAAAGGACACCCGCTGTCTGGGTGCGACTG

CCCAACAATTCCATCGTCACAAACAGCTGATTCGTTTCCTGAAGCGTCTG

GACCGCAACCTGTGGGGTCTGGCGGGCTTGAACTCCTGCCCAGTCAAAGA

AGCGAACCAAAGCACCCTGGAAAACTTCTTGGAGCGTCTGAAAACGATCA

TGAAAGAGAAGTTCCGCAAGTGTAGCAGCGGTGGTAATGGTGGCCACAAG

TGCGACATTACGCTGCAGGAAATCATTAAGACCCTGAACTCTCTGACCGA

GCAGAAAACCCTCTGTACCGAGCTGACGGTGACGGATATCTTTGCGGCGA

GC;
and (cpS4; SEQ ID NO: 28)
ATGGATACCACCGAAAAAGAAACTTTTTGTCGTGCCGCGACTGTCCTGCG

CCAGTTCTACAGCCACCACGAAAAGGACACCCGTTGCCTGGGTGCGACCG

CTCAACAATTCCATCGCCACAAACAGCTGATTCGTTTCCTGAAACGTCTG

GATCGCAACCTGTGGGGTCTGGCGGGTTTGAACAGCTGTCCAGTCAAAGA

-continued
AGCGAACCAGAGCACCCTGGAAAACTTTCTGGAGCGTCTGCGTGTTATCA

TGCAGAGCAAGTGGTTCAAGTGCGGTGCGGGTGGCAATGGTGGCCACAAG

TGTGACATTACCTTGCAAGAGATTATCAAAACGCTGAACTCTCTGACCGA

GCAAAAGACGCTGTGCACCGAGCTGACGGTGACGGACATCTTCGCGGCGT

CC.

IL-13 proteins or IL-13 "protein moieties" include native IL-13 proteins, as well as variant IL-13 proteins. A "native" or "wild type" IL-13 sequence, as used herein, refers to a human IL-13 sequence, whether purified from natural sources or made using recombinant techniques, and including the amino acid sequence (with an additional methionine at the N-terminus) as follows:

(SEQ ID NO: 7)
MPGPVPPSTALRELIEELVNITQNQKAPLCNGSMVWSINLTAGMYCAALE

SLINVSGCSAIEKTQRMLSGFCPHKVSAGQFSSLHVRDTKIEVAQFVK

DLLLHLKKLFREGQFN.

In some embodiments, IL-13 proteins that can be used in the fusion proteins of the present disclosure are variant IL-13 proteins that have increased selectivity for IL-13Rα1 (type II receptor) relative wild-type IL-13 protein. For example, the IL-13 variant sequence may include the amino acid sequence (with an additional methionine at the N-terminus) as follows:

(the "All" variant"; SEQ ID NO: 8)
MPGPVPPSTAVRELIEELINITQNQKAPLCNGSMVWSINRTAGMYCAALE

SLINVSGCSAIEKTQRMLSGFCPHKVSAGQFSSLHVRSSKIEVAQFVKD

LLFHLRTLFREGQFN.

In some embodiment, a variant IL-13 protein that has increased selectivity for IL-13Rα1 (type II receptor) relative wild-type IL-13 protein is an IL-13 protein that includes the following mutations relative to the sequence of native human IL-13 (SEQ ID NO: 7), the numbering excluding the methionine at the N-terminus: L10V/E12A/V18I/R65D/D87S/T88S/L101F/K104R/K105T (the "DN" variant). For example, the IL-13 variant sequence may include the amino acid sequence (with an additional methionine at the N-terminus) as follows:

(SEQ ID NO: 9)
MPGPVPPSTAVRALIEELINITQNQKAPLCNGSMVWSINLTAGMYCAALE

SLINVSGCSAIEKTQDMLSGFSSCPHKVSAGQFLHVRSSKIEVAQFVKD

LLFHLRTLFREGQFN.

In some embodiments, IL-13 proteins that can be used in the fusion proteins of the present disclosure are circularly permuted (cp). In some embodiments, a cpIL-13 protein that can be used in the fusion proteins of the present disclosure includes an IL-13 protein in which residues 44-114 of native human IL-13 (SEQ ID NO: 7) are joined to residues 1-43 with a linker and an initial methionine residue, as follows:

(SEQ ID NO: 10)
MYCAALESLINVSGCSAIEKTQRMLSGFCPHKVSAGQFSSLHVRDTKIE
VAQFVKDLLLHLKKLFREGQFN*GGSG*PGPVPPSTALRELIEELVNITQN
QKAPLCNGSMVWSINLTAG.

In some embodiments, a variant cpIL-13 protein that can be used in the fusion proteins of the present disclosure is as follows:

(SEQ ID NO: 11)
MYCAALESLINVSGCSAIEKTQRMLSGFCPHKVSAGQFSSLHVRDTKIEV
AQFVKDLLLHLKKLFREGQFN*GGSG*MPGPVPPSTALRELIEELVNITQNQ
KAPLCNGSMVWSINLTAG.

In alternative embodiments, a cpIL-13 protein that can be used in the fusion proteins of the present disclosure includes an IL-13 protein in which residues 44-114 of native human IL-13 (SEQ ID NO: 7) are joined to residues 1-43 with a linker and an initial methionine residue, in the context of an "A11" variant, as follows:

(SEQ ID NO: 12)
MYCAALESLINVSGCSAIEKTQRMLSGFCPHKVSAGQFSSLHVRSSKIEV
AQFVKDLLFHLRTLFREGQFN*GGSG*PGPVPPSTAVRELIEELINITQNQK
APLCNGSMVWSINRTAG.

In some embodiments, a variant cpIL-13 protein that can be used in the fusion proteins of the present disclosure is as follows:

(SEQ ID NO: 13)
MYCAALESLINVSGCSAIEKTQRMLSGFCPHKVSAGQFSSLHVRSSKIEV
AQFVKDLLFHLRTLFREGQFN*GGSG*MPGPVPPSTAVRELIEELINITQNQ
KAPLCNGSMVWSINRTAG.

In alternative embodiments, a cpIL-13 protein that can be used in the fusion proteins of the present disclosure includes an IL-13 protein in which residues 44-114 of native human IL-13 (SEQ ID NO: 7) are joined to residues 1-43 with a linker and an initial methionine residue, in the context of a "DN" variant, as follows:

(SEQ ID NO: 14)
MYCAALESLINVSGCSAIEKTQDMLSGFCPHKVSAGQFSSLHVRSSKIEV
AQFVKDLLFHLRTLFREGQFN*GGSG*PGPVPPSTAVRALIEELINITQNQK
APLCNGSMVWSINLTAG.

In some embodiments, a variant cpIL-13 protein that can be used in the fusion proteins of the present disclosure is as follows:

(SEQ ID NO: 15)
MYCAALESLINVSGCSAIEKTQDMLSGFCPHKVSAGQFSSLHVRSSKIEV
AQFVKDLLFHLRTLFREGQFN*GGSG*MPGPVPPSTAVRALIEELINITQNQ
KAPLCNGSMVWSINLTAG.

Exemplary IL-13 proteins that can be used in the fusion proteins of the present disclosure include those described herein, as well as sequences having at least 80% sequence identity, at least 85%, at least 90%, at least 95%, at least 98% or even at least 99% sequence identity to native IL-13 ("variant IL-13 proteins"), as long as the variant IL-13 protein retains the ability to bind the IL-13 receptor, or retains increased selectivity for the IL-13Rα1 (type II receptor) relative to wild-type IL-13 protein, or retains a desired biological activity.

It is to be understood that IL-13 proteins according to the present disclosure include fragments that can be smaller than the native 114 amino acid IL-13 protein, as long as the IL-13 protein fragment retains the ability to bind the IL-13 receptor, or retains increased selectivity for the IL-13Rα1 (type II receptor) relative to wild-type IL-13 protein, or retains a desired biological activity.

It is also to be understood that the present disclosure encompasses nucleic acid molecules (including but not limited to RNA sequences or DNA sequences) that encode an IL-13 protein as described herein or known in the art.

BCL-2 Family Proteins

Bcl-2-related proteins or polypeptides ("Bcl-2 family proteins" or "Bcl-2 family members") are involved in regulation of apoptosis. Bcl-2 family proteins fall into two distinct categories: those that inhibit cell death (the "anti-apoptotic" Bcl-2 family proteins) and those that enhance cell death (the "pro-apoptotic" Bcl-2 family proteins). Bcl-2 family proteins share one to four conserved Bcl-2 homology (BH) domains, designated BH1, BH2, BH3, and BH4.

Anti-apoptotic Bcl-2 family proteins include Bcl-2 itself, Bcl-$x_L$ (Boise et al., Cell 74:597-608, 1993; e.g., GenBank Accession No. Q07817; GenBank Accession No. Z23115), Bcl-w, etc. In some embodiments, a Bcl-$x_L$ protein that can be used in the fusion proteins according to the present disclosure includes a sequence as follows:

(SEQ ID NO: 16)
SQSNRELVVDFLSYKLSQKGYSWSQFSDVEENRTEAPEGTESEMETPSAI
NGNPSWHLADSPAVNGATGHSSSLDAREVIPMAAVKQALREAGDEFELRY
RRAFSDLTSQLHITPGTAYQSFEQVVNELFRDGVNWGRIVAFFSFGGALC
VESVDKEMQVLVSRIAAVVMATYLNDHLEPWIQENGGWDTFVELYGNNAA
AESRKGQERFNRWFLTGMTVAGVVLLGSLFSRK.

In some embodiments, an anti-apoptotic Bcl-2 family protein includes at least a fragment of a Bcl-2 family member, where the anti-apoptotic Bcl-2 family protein or fragment is capable of enhancing cell survival, enhancing cell proliferation, or inhibiting cell death or apoptosis. By "enhancing cell survival" is meant increasing (e.g., by at least 10%, 20%, 30%, or by as much as 50%, 75%, 85% or 90% or more) the probability that a cell at risk of cell death will survive. By "enhancing cell proliferation" is meant increasing (e.g., by at least 10%, 20%, 30%, or by as much as 50%, 75%, 85% or 90% or more) the growth or proliferation of a cell. By "inhibiting cell death or apoptosis" is meant reducing (e.g., by at least 10%, 20%, 30%, or by as much as 50%, 75%, 85% or 90% or more) the probability that a cell at risk of cell death will undergo apoptotic, necrotic, or any other form of cell death. Suitable assays for measuring the enhancement of cell survival, enhancement of cell proliferation, or inhibition of cell death or apoptosis are described herein or known in the art.

It is also to be understood that the present disclosure encompasses nucleic acid molecules that encode an anti-apoptotic Bcl-2 family member protein or fragment thereof, as described herein or known in the art.

Exemplary anti-apoptotic Bcl-2 family member nucleic acid molecules include:

(Variant BclxL; SEQ ID NO: 29)

TCTCAGTCTAACCGCGAACTGGTGGTGGACTTCCTGTCTTATAAACTGAG

CCAGAAAGGCTACTCCTGGAGCCAGTTCAGCGACGTAGAGGAGAACCGTA

CCGAAGCTCCTGAAGGCACCGAGAGCGAGATGGAAACCCCATCCGCGATT

AACGGCAACCCGTCCTGGCACCTGGCTGATTCTCCGGCGGTAAACGGCGC

AACTGGTCATTCTAGCTCCCTGGATGCACGTGAAGTAATCCCGATGGCCG

CGGTTAAACAGGCGCTGCGTGAAGCTGGTGACGAATTTGAGCTGCGCTAC

CGCCGTGCATTTTCTGATCTGACCTCCCAGCTGCACATCACGCCGGGTAC

CGCATACCAAAGCTTCGAACAGGTGGTTAACGAACTGTTTCGTGACGGCG

TCAACTGGGGCCGCATCGTGGCCTTTTTCTCTTTCGGCGGTGCCCTGTGC

GTCGAATCTGTTGACAAAGAAATGCAGGTTCTGGTGAGCCGTATTGCGGC

TTGGATGGCAACTTATCTGAACGATCACCTGGAACCGTGGATCCAGGAAA

ACGGTGGTTGGGATACCTTCGTTGAACTGTACGGTAACAATGCTGCGGCG

GAATCCCGTAAGGGTCAAGAACGTTTCAATCGCTGGTTCCTGACCGGCAT

GACTGTTGCTGGTGTAGTTCTGCTGGGTTCTCTGTTCTCCCGTAAA.

IL-4R Receptor Binding Protein/Anti-Apoptotic Bcl-2 Family Fusion Proteins

"Fusion proteins" according to the present disclosure include IL-4R binding proteins, such as IL-4 and IL-13, joined to an anti-apoptotic Bcl-2 family member, with optional additional sequences or moieties (such as linkers), as described herein, as well as nucleic acid molecules encoding such fusion proteins. Also encompassed are recombinant nucleic acid molecules, in which a nucleic acid sequence encoding a fusion protein is operably linked to a promoter, vectors containing such a molecule, and transgenic cells comprising such a molecule.

IL-4 (including cpIL-4 and IL-4 fragments and variants) can be linked to anti-apoptotic Bcl-2 family polypeptides, as exemplified by Bcl-2, Bcl-$x_L$ or Bcl-w, or fragments or variants thereof, as long as the resulting fusion protein retains anti-apoptotic activity.

Any form or derivative of IL-4 can be used. For example, IL-4 or a fragment of IL-4 that binds to the IL-4 receptor can be used. Additionally, multiple anti-apoptotic Bcl-2 family proteins or fragments or variants thereof can be joined to an IL-4 protein or fragment or variant thereof, or multiple IL-4 proteins or fragments or variants thereof can be joined to an anti-apoptotic Bcl-2 family protein or fragment or variant thereof or multiple anti-apoptotic Bcl-2 family proteins or fragments or variants thereof can be joined to multiple IL-4 proteins or fragments or variants thereof.

IL-13 (including IL-13 fragments or variants) can be linked to anti-apoptotic Bcl-2 family polypeptides, as exemplified by Bcl-2, Bcl-$x_L$ or Bcl-w, or fragments or variants thereof, as long as the resulting fusion protein retains anti-apoptotic activity. Any form or derivative of IL-13 can be used. For example, IL-13 or fragments of IL-13 that bind to the IL-13 receptor can be used. Additionally, multiple anti-apoptotic Bcl-2 family proteins or fragments or variants thereof can be joined to IL-13 or fragments or variants thereof or multiple IL-13 proteins or fragments or variants thereof can be joined to anti-apoptotic Bcl-2 family proteins or fragments or variants thereof.

A cpIL-4, can be linked to an anti-apoptotic Bcl-2 family polypeptides as exemplified by Bcl-2, Bcl-$x_L$ or Bcl-w, as long as the fusion protein retains anti-apoptotic activity, as discussed herein or known in the art. Any form or derivative of cpIL-4 can be used. Additionally, multiple cpIL-4 proteins can be joined to an anti-apoptotic Bcl-2 family protein or multiple anti-apoptotic Bcl-2 family proteins can be joined to cpIL-4 proteins or multiple cpIL-4 proteins can be joined to multiple anti-apoptotic Bcl-2 family proteins.

Exemplary fusion proteins are listed in Table 1.

TABLE 1

IL-4/Bcl-2 Family Fusion Proteins

| Name | Circularly permuted IL-4 | Linker | Bcl-2 Family Protein | Description |
|---|---|---|---|---|
| cpIL4-BclxL | M<u>**D**</u>TTEKETFCRAATVLRQFYSHHEKDTRCLGATAQQFHRHKQLIRFLKRLDRNLWGLAGLNSCPVKEANQSTLENFLERLKTIMREKYSKCSS***GGNGG***HKCDITLQEIIKTLNSLTEQKTLCTELTVTDIFAAS (SEQ ID NO: 2). | KASGGPE (SEQ ID NO: 17). | SQSNRELVVDFLSYKLSQKGYSWSQFSDVEENRTEAPEGTESEMETPSAINGNPSWHLADSPAVNGATGHSSSLDAREVIPMAAVKQALREAGDEFELRYRRAFSDLTSQLHITPGTAYQSFEQVVNELFRDGVNWGRIVAFFSFGGALCVESVDKEMQVLVSRIAAWMATYLNDHLEPWIQENGGWDTFVELYGNNAAAESRKGQERFNRWFLTGMTVAGVVLLGSLFSRK (SEQ ID NO: 16). | IL-4 fused to human BclxL |

Fusion Sequence:
M<u>D</u>TTEKETFCRAATVLRQFYSHHEKDTRCLGATAQQFHRHKQLIRFLKRLDRNLWGLAGLN
SCPVKEANQSTLENFLERLKTIMREKYSKCSS*GGNGG*HKCDITLQEIIKTLNSLTEQKTLCTE
LTVTDIFAASKASGGPESQSNRELVVDFLSYKLSQKGYSWSQFSDVEENRTEAPEGTESEM TABLE 1-continued IL-4/Bcl-2 Family Fusion Proteins

| Name | Circularly permuted IL-4 | Linker | Bcl-2 Family Protein | Description |
|---|---|---|---|---|

ETPSAINGNPSWHLADSPAVNGATGHSSSLDAREVIPMAAVKQALREAGDEFELRYRRAFS
DLTSQLHITPGTAYQSFEQVVNELFRDGVNWGRIVAFFSFGGALCVESVDKEMQVLVSRIAA
WMATYLNDHLEPWIQENGGWDTFVELYGNNAAAESRKGQERFNRWFLTGMTVAGVVLLG
SLFSRK (SEQ ID NO: 18).

Fusion DNA Sequence:
ATGGACACGACTGAGAAAGAGACCTTCTGCCGTGCAGCAACTGTTCTGCGTCAGTTCTA
TTCCCACCACGAAAAAGATACGCGTTGCCTGGGTGCTACTGCGCAGCAGTTCCATCGTC
ATAAGCAACTGATTCGCTTTCTGAAACGTCTGGACCGTAACCTGTGGGGTCTGGCCGGT
CTGAACAGCTGCCCGGTCAAAGAAGCGAACCAGTCCACTCTGGAAAACTTCCTGGAAC
GCCTGAAGACCATCATGCGCGAAAAATACTCCAAGTGTTCCAGCGGCGGCAACGGCGG
TCACAAATGTGACATCACCCTGCAGGAAATCATCAAAACTCTGAATTCTCTGACTGAGCA
GAAAACCCTGTGTACCGAACTGACCGTGACCGATATTTTTGCCGCTTCTAAAGCGTCTG
GTGGCCCGGAATCTCAGTCTAACCGCGAACTGGTGGTGGACTTCCTGTCTTATAAACTG
AGCCAGAAAGGCTACTCCTGGAGCCAGTTCAGCGACGTAGAGGAGAACCGTACCGAAG
CTCCTGAAGGCACCGAGAGCGAGATGGAAACCCCATCCGCGATTAACGGCAACCCGTC
CTGGCACCTGGCTGATTCTCCGGCGGTAAACGGCGCAACTGGTCATTCTAGCTCCCTG
GATGCACGTGAAGTAATCCCGATGGCCGCGGTTAAACAGGCGCTGCGTGAAGCTGGTG
ACGAATTTGAGCTGCGCTACCGCCGTGCATTTTCTGATCTGACCTCCCAGCTGCACATC
ACGCCGGGTACCGCATACCAAAGCTTCGAACAGGTGGTTAACGAACTGTTTCGTGACG
GCGTCAACTGGGGCCGCATCGTGGCCTTTTTCTCTTTCGGCGGTGCCCTGTGCGTCGA
ATCTGTTGACAAAGAAATGCAGGTTCTGGTGAGCCGTATTGCGGCTTGGATGGCAACTT
ATCTGAACGATCACCTGGAACCGTGGATCCAGGAAAACGGTGGTTGGGATACCTTCGTT
GAACTGTACGGTAACAATGCTGCGGCGGAATCCCGTAAGGGTCAAGAACGTTTCAATC
GCTGGTTCCTGACCGGCATGACTGTTGCTGGTGTAGTTCTGCTGGGTTCTCTGTTCTCC
CGTAAA (SEQ ID NO: 30).

| Name | Circularly permuted IL-4 | Linker | Bcl-2 Family Protein | Description |
|---|---|---|---|---|
| coIL4-Ub-BclxL | MDTTEKETFCRAAT VLRQFYSHHEKDTR CLGATAQQFHRHK QLIRFLKRLDRNLW GLAGLNSCPVKEAN QSTLENFLERLKTIM REKYSKCSS***GGNGG*** HKCDITLQEIIKTL NSLTEQKTLCTELT VTDIFAAS (SEQ ID NO: 2). | GGGSMQIF VRTLTGRTI TLEVEPSDT IENVRARIQ DREGIPPDQ QRLIFAGRQ LEDGRTLSD YNIQRESTL HLVLRLRG GGS (SEQ ID NO: 19). | SQSNRELVVDFLS YKLSQKGYSWSQ FSDVEENRTEAPE GTESEMETPSAIN GNPSWHLADSPA VNGATGHSSSLDA REVIPMAAVKQAL REAGDEFELRYRR AFSDLTSQLHITPG TAYQSFEQVVNEL FRDGVNWGRIVAF FSFGGALCVESVD KEMQVLVSRIAAW MATYLNDHLEPWI QENGGWDTFVEL YGNNAAAESRKG QERFNRWFLTGM TVAGVVLLGSLFS RK (SEQ ID NO: 16). | Circularly permuted human IL-4 fused to human BclxL via a Ubiquitin linker |

Fusion Sequence:
MDTTEKETFCRAATVLRQFYSHHEKDTRCLGATAQQFHRHKQLIRFLKRLDRNLWGLAGLN
SCPVKEANQSTLENFLERLKTIMREKYSKCSS*GGNGG*HKCDITLQEIIKTLNSLTEQKTLCTE
LTVTDIFAASGGGSMQIFVRTLTGRTITLEVEPSDTIENVRARIQDREGIPPDQQRLIFAGRQL
EDGRTLSDYNIQRESTLHLVLRLRGGGSSQSNRELVVDFLSYKLSQKGYSWSQFSDVEENR
TEAPEGTESEMETPSAINGNPSWHLADSPAVNGATGHSSSLDAREVIPMAAVKQALREAGD
EFELRYRRAFSDLTSQLHITPGTAYQSFEQVVNELFRDGVNWGRIVAFFSFGGALCVESVD
KEMQVLVSRIAAWMATYLNDHLEPWIQENGGWDTFVELYGNNAAAESRKGQERFNRWFLT
GMTVAGVVLLGSLFSRK (SEQ ID NO: 20).

Fusion DNA Sequence:
ATGGACACGACTGAGAAAGAGACCTTCTGCCGTGCAGCAACTGTTCTGCGTCAGTTCTA
TTCCCACCACGAAAAAGATACGCGTTGCCTGGGTGCTACTGCGCAGCAGTTCCATCGTC
ATAAGCAACTGATTCGCTTTCTGAAACGTCTGGACCGTAACCTGTGGGGTCTGGCCGGT
CTGAACAGCTGCCCGGTCAAAGAAGCGAACCAGTCCACTCTGGAAAACTTCCTGGAAC
GCCTGAAGACCATCATGCGCGAAAAATACTCCAAGTGTTCCAGCGGCGGCAACGGCGG
TCACAAATGTGACATCACCCTGCAGGAAATCATCAAAACTCTGAATTCTCTGACTGAGCA
GAAAACCCTGTGTACCGAACTGACCGTGACCGATATTTTTGCCGCTTCTAAAGGTGGCG
GCTCTATGCAAATTTTCGTTCGTACCCTGACGGGTCGTACCATCACTCTGGAAGTAGAA
CCGAGCGACACGATCGAAAATGTCCGCGCACGCATCCAAGACCGCGAAGGCATTCCAC
CGGATCAGCAGCGTCTGATCTTCGCCGGTCGCCAGCTGGAGGATGGTCGTACTCTGTC
CGATTATAACATCCAGCGTGAATCCACCCTGCACCTGGTGCTGCGTCTGCGTGGCGGT
GGTAGCTCTCAGTCTAACCGCGAACTGGTGGTGGACTTCCTGTCTTATAAACTGAGCCA
GAAAGGCTACTCCTGGAGCCAGTTCAGCGACGTAGAGGAGAACCGTACCGAAGCTCCT
GAAGGCACCGAGAGCGAGATGGAAACCCCATCCGCGATTAACGGCAACCCGTCCTGG
CACCTGGCTGATTCTCCGGCGGTAAACGGCGCAACTGGTCATTCTAGCTCCCTGGATG
CACGTGAAGTAATCCCGATGGCCGCGGTTAAACAGGCGCTGCGTGAAGCTGGTGACGA TABLE 1-continued IL-4/Bcl-2 Family Fusion Proteins

| Name | Circularly permuted IL-4 | Linker | Bcl-2 Family Protein | Description |
| --- | --- | --- | --- | --- |
| ATTTGAGCTGCGCTACCGCCGTGCATTTTCTGATCTGACCTCCCAGCTGCACATCACGC<br>CGGGTACCGCATACCAAAGCTTCGAACAGGTGGTTAACGAACTGTTTCGTGACGGCGT<br>CAACTGGGGCCGCATCGTGGCCTTTTTCTCTTTCGGCGGTGCCCTGTGCGTCGAATCT<br>GTTGACAAAGAAATGCAGGTTCTGGTGAGCCGTATTGCGGCTTGGATGGCAACTTATCT<br>GAACGATCACCTGGAACCGTGGATCCAGGAAAACGGTGGTTGGGATACCTTCGTTGAA<br>CTGTACGGTAACAATGCTGCGGCGGAATCCCGTAAGGGTCAAGAACGTTTCAATCGCT<br>GGTTCCTGACCGGCATGACTGTTGCTGGTGTAGTTCTGCTGGGTTCTCTGTTCTCCCGT<br>AAA (SEQ ID NO: 31). | | | | |
| cpKFR4-<br>Ub-BclxL | MDTTEKETFCRAAT<br>VLRQFYSHHEKDTR<br>CLGATAQQFHRHK<br>QLIRFLKRLDRNLW<br>GLAGLNSCPVKEAN<br>QSTLENFLERLKTIM<br>KEKFRKCSSGGNGG<br>HKCDITLQEIIKTLN<br>SLTEQKTLCTELTVT<br>DIFAAS (SEQ ID<br>NO: 5). | GGGSMQIF<br>VRTLTGRTI<br>TLEVEPSDT<br>IENVRARIQ<br>DREGIPPDQ<br>QRLIFAGRQ<br>LEDGRTLSD<br>YNIQRESTL<br>HLVLRLRG<br>GGS (SEQ<br>ID NO: 19). | SQSNRELVVDFLS<br>YKLSQKGYSWSQ<br>FSDVEENRTEAPE<br>GTESEMETPSAIN<br>GNPSWHLADSPA<br>VNGATGHSSSLDA<br>REVIPMAAVKQAL<br>REAGDEFELRYRR<br>AFSDLTSQLHITPG<br>TAYQSFEQVVNEL<br>FRDGVNWGRIVAF<br>FSFGGALCVESVD<br>KEMQVLVSRIAAW<br>MATYLNDHLEPWI<br>QENGGWDTFVEL<br>YGNNAAAESRKG<br>QERFNRWFLTGM<br>TVAGVVLLGSLFS<br>RK (SEQ ID No:<br>16). | Circularly<br>permuted KFR<br>variant of human<br>IL-4 fused to<br>human BclxL via a<br>Ubiquitin linker |
| Fusion Sequence:<br>MDTTEKETFCRAATVLRQFYSHHEKDTRCLGATAQQFHRHKQLIRFLKRLDRNLWGLAGLN<br>SCPVKEANQSTLENFLERLKTIMKEKFRKCSSGGNGGHKCDITLQEIIKTLNSLTEQKTLCTE<br>LTVTDIFAASGGGSMQIFVRTLTGRTITLEVEPSDTIENVRARIQDREGIPPDQQRLIFAGRQL<br>EDGRTLSDYNIQRESTLHLVLRLRGGGSSQSNRELVVDFLSYKLSQKGYSWSQFSDVEENR<br>TEAPEGTESEMETPSAINGNPSWHLADSPAVNGATGHSSSLDAREVIPMAAVKQALREAGD<br>EFELRYRRAFSDLTSQLHITPGTAYQSFEQVVNELFRDGVNWGRIVAFFSFGGALCVESVD<br>KEMQVLVSRIAAWMATYLNDHLEPWIQENGGWDTFVELYGNNAAAESRKGQERFNRWFLT<br>GMTVAGVVLLGSLFSRK (SEQ ID NO: 21). | | | | |
| cpKFR4-<br>BclxL | MDTTEKETFCRAAT<br>VLRQFYSHHEKDTR<br>CLGATAQQFHRHK<br>QLIRFLKRLDRNLW<br>GLAGLNSCPVKEAN<br>QSTLENFLERLKTIM<br>KEKFRKCSSGGNGG<br>HKCDITLQEIIKTLN<br>SLTEQKTLCTELTVT<br>DIFAAS (SEQ ID<br>NO: 5). | GS | SQSNRELVVDFLS<br>YKLSQKGYSWSQ<br>FSDVEENRTEAPE<br>GTESEMETPSAIN<br>GNPSWHLADSPA<br>VNGATGHSSSLDA<br>REVIPMAAVKQAL<br>REAGDEFELRYRR<br>AFSDLTSQLHITPG<br>TAYQSFEQVVNEL<br>FRDGVNWGRIVAF<br>FSFGGALCVESVD<br>KEMQVLVSRIAAW<br>MATYLNDHLEPWI<br>QENGGWDTFVEL<br>YGNNAAAESRKG<br>QERFNRWFLTGM<br>TVAGVVLLGSLFS<br>RK (SEQ ID NO:<br>16). | Circularly<br>permuted KFR<br>variant of human<br>IL-4 fused to<br>human BclxL via a<br>GS linker |
| Fusion Sequence:<br>MDTTEKETFCRAATVLRQFYSHHEKDTRCLGATAQQFHRHKQLIRFLKRLDRNLWGLAGLN<br>SCPVKEANQSTLENFLERLKTIMKEKFRKCSSGGNGGHKCDITLQEIIKTLNSLTEQKTLCTE<br>LTVTDIFAASKGSSQSNRELVVDFLSYKLSQKGYSWSQFSDVEENRTEAPEGTESEMETPS<br>AINGNPSWHLADSPAVNGATGHSSSLDAREVIPMAAVKQALREAGDEFELRYRRAFSDLTS<br>QLHITPGTAYQSFEQVVNELFRDGVNWGRIVAFFSFGGALCVESVDKEMQVLVSRIAAWMA<br>TYLNDHLEPWIQENGGWDTFVELYGNNAAAESRKGQERFNRWFLTGMTVAGVVLLGSLFS<br>RK (SEQ ID NO: 22). | | | | |
| cpS4-Ub-<br>BclxL | MDTTEKETFCRAAT<br>VLRQFYSHHEKDTR<br>CLGATAQQFHRHK<br>QLIRFLKRLDRNLW<br>GLAGLNSCPVKEAN | GGGSMQIF<br>VRTLTGRTI<br>TLEVEPSDT<br>IENVRARIQ<br>DREGIPPDQ | SQSNRELVVDFLS<br>YKLSQKGYSWSQ<br>FSDVEENRTEAPE<br>GTESEMETPSAIN<br>GNPSWHLADSPA | Circularly<br>permuted RGA<br>(Super-4) variant<br>of human IL-4<br>fused to human |

TABLE 1-continued

IL-4/Bcl-2 Family Fusion Proteins

| Name | Circularly permuted IL-4 | Linker | Bcl-2 Family Protein | Description |
|---|---|---|---|---|
| | QSTLENFLERL**RV**IM **QS**K**WF**KC**GA***GGNGG* HKCDITLQEIIKTLN SLTEQKTLCTELTVT DIFAASK (SEQ ID NO: 4). | QRLIFAGRQ LEDGRTLSD YNIQRESTL HLVLRLRG GGS (SEQ ID NO: 19). | VNGATGHSSSLDA REVIPMAAVKQAL REAGDEFELRYRR AFSDLTSQLHITPG TAYQSFEQVVNEL FRDGVNWGRIVAF FSFGGALCVESVD KEMQVLVSRIAAW MATYLNDHLEPWI QENGGWDTFVEL YGNNAAAESRKG QERFNRWFLTGM TVAGVVLLGSLFS RK (SEQ ID NO: 16). | BclxL via a Ubiquitin linker |
| Fusion Sequence:<br>M**D**TTEKETFCRAATVLRQFYSHHEKDTRCLGATAQQFHRHKQLIRFLKRLDRNLWGLAGLN<br>SCPVKEANQSTLENFLERL**RV**IM**QS**K**WF**KC**GA***GGNGG*HKCDITLQEIIKTLNSLTEQKTLCT<br>ELTVTDIFAASKGGGSMQIFVRTLTGRTITLEVEPSDTIENVRARIQDREGIPPDQQRLIFAGR<br>QLEDGRTLSDYNIQRESTLHLVLRLRGGGSSQSNRELVVDFLSYKLSQKGYSWSQFSDVEE<br>NRTEAPEGTESEMETPSAINGNPSWHLADSPAVNGATGHSSSLDAREVIPMAAVKQALREA<br>GDEFELRYRRAFSDLTSQLHITPGTAYQSFEQVVNELFRDGVNWGRIVAFFSFGGALCVES<br>VDKEMQVLVSRIAAWMATYLNDHLEPWIQENGGWDTFVELYGNNAAAESRKGQERFNRW<br>FLTGMTVAGVVLLGSLFSRK (SEQ ID NO: 23). | | | | |
| cpS4-BclxL | M**D**TTEKETFCRAAT VLRQFYSHHEKDTR CLGATAQQFHRHK QLIRFLKRLDRNLW GLAGLNSCPVKEAN QSTLENFLERL**RV**IM **QS**K**WF**KC**GA***GGNGG* HKCDITLQEIIKTLN SLTEQKTLCTELTVT DIFAASK (SEQ ID NO: 4). | GS | SQSNRELVVDFLS YKLSQKGYSWSQ FSDVEENRTEAPE GTESEMETPSAIN GNPSWHLADSPA VNGATGHSSSLDA REVIPMAAVKQAL REAGDEFELRYRR AFSDLTSQLHITPG TAYQSFEQVVNEL FRDGVNWGRIVAF FSFGGALCVESVD KEMQVLVSRIAAW MATYLNDHLEPWI QENGGWDTFVEL YGNNAAAESRKG QERFNRWFLTGM TVAGVVLLGSLFS RK (SEQ ID NO 16). | Circularly permuted RGA (Super-4) variant of human IL-4 fused to human BclxL via a GS linker |
| Fusion Sequence:<br>M**D**TTEKETFCRAATVLRQFYSHHEKDTRCLGATAQQFHRHKQLIRFLKRLDRNLWGLAGLN<br>SCPVKEANQSTLENFLERL**RV**IM**QS**K**WF**KC**GA***GGNGG*HKCDITLQEIIKTLNSLTEQKTLCT<br>ELTVTDIFAASKGSSQSNRELVVDFLSYKLSQKGYSWSQFSDVEENRTEAPEGTESEMETP<br>SAINGNPSWHLADSPAVNGATGHSSSLDAREVIPMAAVKQALREAGDEFELRYRRAFSDLT<br>SQLHITPGTAYQSFEQVVNELFRDGVNWGRIVAFFSFGGALCVESVDKEMQVLVSRIAAWM<br>ATYLNDHLEPWIQENGGWDTFVELYGNNAAAESRKGQERFNRWFLTGMTVAGVVLLGSLF<br>SRK (SEQ ID NO: 24). | | | | |

The joining or "fusion" of an IL-4R binding protein, such as IL-4 or IL-13, to an anti-apoptotic Bcl-2 family member may be direct, such that one portion of the IL-4R binding protein is directly attached to a portion of the anti-apoptotic Bcl-2 family member. For example, one end of the amino acid sequence of an IL-4R binding protein can be directly attached to an end of the amino acid sequence of the anti-apoptotic Bcl-2 family member. For example, the C-terminus of the IL-4R binding protein can be linked to the N-terminus of the anti-apoptotic Bcl-2 family member, or the C-terminus of the anti-apoptotic Bcl-2 family member can be linked to the N-terminus of the IL-4R binding protein. Methods of generating such fusion proteins are routine in the art, for example using recombinant molecular biology methods.

Linkers

In some embodiments, an IL-4R binding protein moiety can be linked to the anti-apoptotic Bcl-2 family member moiety indirectly through a linker. The linker can serve, for example, simply as a convenient way to link the two moieties, as a means to spatially separate the two moieties, to provide an additional functionality to the IL-4R binding protein or the anti-apoptotic Bcl-2 family member, or a combination thereof.

In general, the linker joining the IL-4R binding protein moiety and the anti-apoptotic Bcl-2 family member moiety can be designed to (1) allow the two molecules to fold and act independently of each other, (2) not have a propensity for developing an ordered secondary structure which could interfere with the functional domains of the two moieties, (3)

have minimal hydrophobic or charged characteristics which could interact with the functional protein domains and/or (4) provide steric separation of the two regions. For example, in some instances, it may be desirable to spatially separate the IL-4R binding protein and the anti-apoptotic Bcl-2 family member to prevent the IL-4R binding protein from interfering with the activity of the anti-apoptotic Bcl-2 family member and/or the anti-apoptotic Bcl-2 family member interfering with the activity of the IL-4R binding protein. The linker can also be used to provide, for example, lability to the connection between the IL-4R binding protein and the anti-apoptotic Bcl-2 family member, an enzyme cleavage site (for example, a cleavage site for a protease), a stability sequence, a molecular tag, a detectable label, or various combinations thereof. In some embodiments, a linker can be present between two domains of an IL-4R binding protein (such as in a cp molecule) or anti-apoptotic Bcl-2 family member.

The linker can be bifunctional or polyfunctional, i.e., contain at least about a first reactive functionality at, or proximal to, a first end of the linker that is capable of bonding to, or being modified to bond to, the IL-4R binding protein and a second reactive functionality at, or proximal to, the opposite end of the linker that is capable of bonding to, or being modified to bond to, the anti-apoptotic Bcl-2 family member being modified. The two or more reactive functionalities can be the same (i.e. the linker is homobifunctional) or they can be different (i.e. the linker is heterobifunctional).

The length and composition of a linker can be varied considerably. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the activity of the IL-4R binding protein and/or anti-apoptotic Bcl-2 family member.

Linkers suitable for use in a fusion protein according to the present disclosure include peptides. The linker can be attached to the IL-4R binding moiety and/or the anti-apoptotic Bcl-2 family member moiety using recombinant DNA technology. Such methods are well-known in the art and details of this technology can be found, for example, in Sambrook, et al. Molecular Cloning: A Laboratory Manual. $2^{nd}$ ed., Cold Spring Harbor Laboratory, Cold Spring Harbor Laboratory Press, Cold Spring Harbor, N.Y., 1989 or Ausubel et al. Current Protocols in Molecular Biology, John Wiley & Sons, 1994) or updates thereto.

The linker peptides can have a chain length of 1 to 500 amino acid residues (such as 1 to 100, 1 to 50, 6 to 30, 1 to 40, 1 to 20, or less than 30 amino acids or 5 to 10 amino acids). In some embodiments, a linker can be 2, 3, 4, 5, 6, 7, or 8 amino acids in length, or can be about 10, 20, 30, 40 or 50 amino acids in length.

Typically, surface amino acids in flexible protein regions include Gly, Asn and Ser, and such amino acids can be used in linker sequences. Other neutral amino acids, such as Thr and Ala, can also be used in the linker sequence. Additional amino acids can be included in the linker to provide unique restriction sites in the linker sequence to facilitate construction of the fusions. In some embodiments, a linker may for instance include the amino acid sequence Gly-Ser (GS) or may be the amino acid sequence Gly-Ser (GS) or may include a ubiquitin sequence:

(SEQ ID NO: 19)
GGGSMQIFVRTLTGRTITLEVEPSDTIENVRARIQDREGIPPDQQRLIFA

GRQLEDGRTLSDYNIQRESTLHLVLRLRGGGS or variant thereof. Ubiquitin molecules suitable for use as linkers are described in, for example, Bachran, C. et al. "Anthrax toxin-mediated delivery of the *Pseudomonas* exotoxin A enzymatic domain to the cytosol of tumor cells via cleavable ubiquitin fusions MBio. 2013 Apr. 30; 4(3): e00201-13, or in PCT publication WO/2012/139112.

Peptide linkers that are susceptible to cleavage by enzymes of the complement system, urokinase, tissue plasminogen activator, trypsin, plasmin, or another enzyme having proteolytic activity may be used in one example. According to another example, the IL-4R binding protein can be attached via a linker susceptible to cleavage by enzymes having a proteolytic activity such as a urokinase, a tissue plasminogen activator, plasmin, thrombin or trypsin. In addition, the IL-4R binding protein can be attached to the anti-apoptotic Bcl-2 family member via disulfide bonds (for example, the disulfide bonds on a cysteine molecule).

The linker can be attached to the IL-4R binding protein moiety and/or anti-apoptotic Bcl-2 family member moiety using routine techniques as known in the art.

Preparation of IL-4R Binding Protein/Anti-apoptotic Bcl-2 Family Fusion Proteins Fusion proteins can be prepared using routine methods as known in the art. Fusion proteins, as well as modifications thereto, can be made, for example, by engineering the nucleic acid encoding the fusion protein using recombinant DNA technology or by peptide synthesis. Modifications to the fusion protein may be made, for example, by modifying the fusion protein polypeptide itself, using chemical modifications and/or limited proteolysis. Combinations of these methods may also be used to prepare the fusion proteins.

Methods of cloning and expressing proteins are well-known in the art, detailed descriptions of techniques and systems for the expression of recombinant proteins can be found, for example, in Current Protocols in Protein Science (Coligan, J. E., et al., Wiley & Sons, New York). Those skilled in the art will understand that a wide variety of expression systems can be used to provide the recombinant protein. Accordingly, the fusion proteins can be produced in a prokaryotic host (e.g., *E. coli, A. salmonicida* or *B. subtilis*) or in a eukaryotic host (e.g., *Saccharomyces* or *Pichia*; mammalian cells, e.g., COS, NIH 3T3, CHO, BHK, 293, or HeLa cells; or insect cells (baculovirus)). The fusion proteins can be purified from the host cells using standard techniques known in the art.

Sequences for various exemplary fusion proteins are provided in Table 1. Variants and homologs of these sequences can be cloned, if an alternative sequence is desired, using standard techniques (see, for example, Ausubel et al., Current Protocols in Molecular Biology, Wiley & Sons, NY (1997 and updates); Sambrook et al., Sambrook, et al. Molecular Cloning: A Laboratory Manual. $2^{nd}$ ed., Cold Spring Harbor Laboratory, Cold Spring Harbor Laboratory Press, Cold Spring Harbor, N.Y., 1989 or updates thereto). For example, the nucleic acid sequence can be obtained directly from a suitable organism, such as *Aeromonas hydrophila*, by extracting mRNA and then synthesizing cDNA from the mRNA template (for example by RT-PCR) or by PCR-amplifying the gene from genomic DNA. Alternatively, the nucleic acid sequence encoding the IL-4R binding moiety or the anti-apoptotic Bcl-2 family moiety can be obtained from an appropriate cDNA library by standard procedures. The isolated cDNA is then inserted into a suitable vector, such as a cloning vector or an expression vector.

Mutations (if desired) can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence.

The expression vector can further include regulatory elements, such as transcriptional elements, required for efficient transcription of the fusion protein-encoding sequences. Examples of regulatory elements that can be incorporated into the vector include, but are not limited to, promoters, enhancers, terminators, and polyadenylation signals. Vectors that include a regulatory element operatively linked to a nucleic acid sequence encoding a genetically engineered fusion protein can be used to produce the fusion protein.

The expression vector may additionally contain heterologous nucleic acid sequences that facilitate the purification of the expressed fusion protein, such as affinity tags such (e.g., metal-affinity tags, histidine tags, avidin/streptavidin encoding sequences, glutathione-S-transferase (GST) encoding sequences, maltose binding protein (MBP) encoding sequences and biotin encoding sequences). In one example, such tags are attached to the N- or C-terminus of a fusion protein, or can be located within the fusion protein. The tags can be removed from the expressed fusion protein prior to use according to methods known in the art. Alternatively, the tags can be retained on the fusion protein, providing that they do not interfere with the ability of the desired activity of the fusion protein.

The fusion protein can include one or more linkers, as well as other moieties, as desired and/or as discussed herein. These can include a binding region, such as avidin or an epitope, or a tag such as a polyhistidine tag, which can be useful for purification and processing of the fusion protein, as well as other linkers as described herein. In addition, detectable markers can be attached to the fusion protein, so that the traffic of the fusion protein through a body or cell can be monitored conveniently. Such markers include radionuclides, enzymes, fluorophores, chromophores, and the like.

One of ordinary skill in the art will appreciate that the DNA can be altered in numerous ways without affecting the biological activity of the encoded protein. For example, PCR can be used to produce variations in the DNA sequence which encodes a fusion protein. Such variations in the DNA sequence encoding a fusion protein can be used to optimize for codon preference in a host cell used to express the protein, or may contain other sequence changes that facilitate expression.

A covalent linkage of an IL-4R binding protein directly to an anti-apoptotic Bcl-2 family member or via a linker may take various forms as is known in the art. For example, the covalent linkage may be in the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Assays

Fusion proteins can be assayed using standard techniques known in the art or described herein.

For example, the ability of the fusion proteins to enhance cell survival or enhance cell proliferation can be assayed in vitro using suitable cells, typically a cell line expressing the target or a cancer cell. In general, cells of the selected test cell line are grown to an appropriate density and the candidate fusion protein is added. The fusion protein can be added to the culture at around at least 1 ng/mL, at least 1 ug/mL, or at least 1 mg/mL, such as from about 0.01 ug/mL to about 1 mg/mL, from about 0.10 ug/mL to about 0.5 mg/mL, from about 1 ug/mL to about 0.4 mg/mL. In some examples, serial dilutions are tested. After an appropriate incubation time (for example, about 48 to 72 hours), cell survival, proliferation or growth is assessed. Methods of determining cell survival, proliferation or growth are well known in the art and include, but are not limited to, the resazurin reduction test (see Fields & Lancaster Am. Biotechnol. Lab., 11:48-50, 1993; O'Brien et al., Eur. J. Biochem., 267:5421-5426, 2000 or U.S. Pat. No. 5,501,959), the sulforhodamine assay (Rubinstein et al., J. Natl. Cancer Inst., 82:113-118, 1999) or the neutral red dye test (Kitano et al., Euro. J. Clin. Investg., 21:53-58, 1991; West et al., J. Investigative Derm., 99:95-100, 1992) or trypan blue assay. Numerous commercially available kits may also be used, for example the CellTiter 96® AQueous One Solution Cell Proliferation Assay (Promega). Proliferation is determined by comparison of cell survival in the treated culture with cell survival in one or more control cultures, for example, untreated cultures and/or cultures pre-treated with a control compound (typically a known therapeutic), or other appropriate control.

Additional assays are described in, for example, Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

Assays for measuring cell apoptosis are known in the art. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

A variety of cell lines suitable for testing the candidate fusion proteins are known in the art and many are commercially available (for example, from the American Type Culture Collection, Manassas, Va.). Similarly, animal models are known in the art and many are commercially available.

Therapeutic Indications and Uses

The fusion proteins including IL-4R binding protein and an anti-apoptotic Bcl-2 family member, as described herein, can be used for a variety of therapeutic purposes. In general, the fusion proteins described herein can be used in the treatment or prophylaxis of any disease, disorder or condition which involves cells which express an IL-4R, and which would be benefited by enhancing cell survival, enhancing cell proliferation, inhibiting cell death or apoptosis, protecting against cell death, increasing cell activation or promoting cell maturation. In some embodiments, the fusion proteins described herein can be used in the treatment or prophylaxis of any disease, disorder or condition which involves cells which express a Type I or Type II IL-4R, and in which selection of one type of receptor over the other is useful, and which would be benefited by enhancing cell survival, enhancing cell proliferation, inhibiting cell death or apoptosis, protecting against cell death, increasing cell activation or promoting cell maturation.

In some embodiments, a fusion protein including an anti-apoptotic Bcl-2 family member can be used to enhance cell proliferation or treat a disease, disorder or condition associated with cell death or apoptosis, such as hypoxia, ischemia, reperfusion, neurodegenerative disorders or conditions affecting the central nervous system ("CNS disorders," for example, stroke, Alzheimer disease, Parkinson's disease, Lou Gehrig's disease, Huntington's chorea, spinal muscular atrophy, transient ischemic neuronal injury such as spinal cord injury, traumatic brain injury, etc.), autoimmune disorders (e.g., Addison's disease, celiac disease, dermatomyositis, Graves disease, Hashimoto's disease, multiple sclerosis, Myasthenia gravis, pernicious anemia, reactive arthritis, rheumatoid arthritis, Sjogren syndrome, systemic lupus erythematosus, Type 1 diabetes, etc.), receipt of a cell, tissue or organ transplantation, cytotoxic drug treatment, receipt of chemotherapy, or receipt of radiation therapy. In some embodiments, a fusion protein including an anti-apoptotic Bcl-2 family member can be used to stimulate lipid cell metabolism to reduce obesity in subjects in need thereof. In some embodiments, a fusion protein including an anti-apoptotic Bcl-2 family member can be used to treat mitochondrial diseases.

Other examples of proliferative and/or differentiative disorders that can be treated using a fusion protein including an anti-apoptotic Bcl-2 family member include skin disorders, inflammatory disorders, etc.

The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

Patients amenable to treatment may also have psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

Other examples of disorders or conditions that can be treated using a fusion protein including an anti-apoptotic Bcl-2 family member include cystitis, wound repair, tendon repair, liver regeneration, liver transplantation, myasthenia gravis, uveitis, Behcet's disease, schistosomiasis, leishmaniasis, tuberculosis, toxoplasmic encephalitis, or malaria.

Other examples of disorders or conditions that can be treated using a fusion protein including an anti-apoptotic Bcl-2 family member include CNS degenerative diseases, epilepsy, amyotrophic lateral sclerosis, Alzheimer's disease, Parkinson's disease, traumatic brain injury, cerebral ischemia, vascular dementia, stroke, multiple sclerosis, spinal cord injury, spinal muscular atrophy, ophthalmic disease or injury, mitochondrial diseases, autoimmune diseases, rheumatoid arthritis, osteoarthritis, osteoporosis, Crohn's disease, atopic dermatitis, psoriasis, inflamatory bowel disease, insulitis, type 1 diabetes, liver transplantation, or lupus. In some embodiments, disorders or conditions that can be treated using a fusion protein including an anti-apoptotic Bcl-2 family member include neurological disorders and conditions, such as CNS degenerative diseases, epilepsy, amyotrophic lateral sclerosis, Alzheimer's disease, Parkinson's disease, traumatic brain injury, cerebral ischemia, vascular dementia, stroke, multiple sclerosis, spinal cord injury, spinal muscular atrophy, etc.

In alternative embodiments, a fusion protein including an anti-apoptotic Bcl-2 family member can be used: as an adjuvant for vaccines used to treat infectious diseases, for ex vivo preservation and expansion of pancreatic islet cells, for ex vivo use for organ preservation, for dendritic cell based therapies, for cancer immunotherapy, for immunomodulation of vaccines, for dendritic cell maturation, or to propagate and expand engineered T cells for, for example, adoptive cell transfer therapy and chimeric antigen receptor (CAR) therapy (CAR-T).

In alternative embodiments, a fusion protein including an anti-apoptotic Bcl-2 family member can be used to stimulate dendritic cells or cell-based vaccines. In alternative embodiments, a fusion protein including an anti-apoptotic Bcl-2 family member can be used as vaccine adjuvants for example for cancer therapy or the treatment of infectious diseases. In alternative embodiments, a fusion protein including an anti-apoptotic Bcl-2 family member can be used to stimulate the immune system, for example, in the treatment of infectious diseases or transplantation.

In some embodiments, a fusion protein including an anti-apoptotic Bcl-2 family protein, or fragment thereof, is capable of enhancing cell survival, enhancing cell proliferation, or inhibiting cell death or apoptosis. In some embodiments, the IL-4R binding protein-anti-apoptotic Bcl-2 family fusion protein is capable of enhancing cell survival, enhancing cell proliferation, or inhibiting cell death or apoptosis, when compared to a suitable control, such as IL-4 alone, IL-4 joined to a non-anti-apoptotic Bcl-2 family protein, etc. A suitable control may also include a previously-established standard. Accordingly, any test or assay for determining the activity or efficacy of an IL-4R binding protein-anti-apoptotic Bcl-2 family fusion protein may be compared to the established standard and it may not be necessary to include a control for comparison each time. By "enhancing cell survival" is meant increasing (e.g., by at least 10%, 20%, 30%, or by as much as 50%, 75%, 85% or 90% or more) the probability that a cell at risk of cell death will survive. By "enhancing cell proliferation" is meant increasing (e.g., by at least 10%, 20%, 30%, or by as much as 50%, 75%, 85% or 90% or more) the growth or proliferation of a cell. By "inhibiting cell death or apoptosis" or "protecting against cell death" is meant reducing (e.g., by at least 10%, 20%, 30%, or by as much as 50%, 75%, 85% or 90% or more) the probability that a cell at risk of cell death will undergo apoptotic, necrotic, or any other form of cell death. By "increasing cell activation" is meant increasing (e.g., by at least 10%, 20%, 30%, or by as much as 50%, 75%, 85% or 90% or more) the activation of a cell. By "promoting cell maturation" is meant increasing (e.g., by at least 10%, 20%, 30%, or by as much as 50%, 75%, 85% or 90% or more) the differentiation of a cell into more mature cell types.

In some embodiments, a fusion protein including an anti-apoptotic Bcl-2 family protein, or fragment thereof, is capable of enhancing cell survival, enhancing cell proliferation, or inhibiting cell death or apoptosis by at least 20%, 30%, or by as much as 50%, 75%, 85% or 90% or more, when compared to a cell cultured under similar conditions but not contacted with the fusion protein.

In some embodiments, a fusion protein including an anti-apoptotic Bcl-2 family protein, or fragment thereof, is capable of enhancing cell survival, enhancing cell proliferation, inhibiting cell death or apoptosis, protecting against cell death, increasing cell activation or promoting cell maturation by at least 20%, 30%, or by as much as 50%, 75%, 85% or 90% or more, compared to native IL-4, when administered at concentrations ranging from about 10 ng/mL to about 10,000 ng/mL, or any value therebetween, such as about 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1500 ng/mL, 2000 ng/mL, 2500 ng/mL, 3000 ng/mL, 3500 ng/mL, 4000 ng/mL, 4500 ng/mL, 5000 ng/mL, 5500 ng/mL, 6000 ng/mL, 6500 ng/mL, 7000 ng/mL, 7500 ng/mL, 8000 ng/mL, 8500 ng/mL, 9000 ng/mL, 9500 ng/mL, or 10000 ng/mL.

Suitable assays for measuring the enhancement of cell survival, enhancement of cell proliferation, inhibition of cell death or apoptosis, protection against cell death, increase of cell activation or promotion of cell maturation are described herein or known in the art.

"Target cells" include, without limitation, neurons, lymphocytes, stem cells, epithelial cells, immune cells, bone cells, apoptotic cells, necrotic cells, lipid cells and others, such as cells undergoing, or at risk of undergoing, apoptosis or necrosis. The target cell chosen will depend on the disease or injury or condition the fusion protein is intended to treat.

Pharmaceutical Compositions, Dosages and Administration

Pharmaceutical compositions according to the present disclosure can include one or more fusion proteins and one or more non-toxic, pharmaceutically-acceptable carriers, diluents, excipients and/or adjuvants. Such compositions can be suitable for use in treatment of therapeutic indications as described herein.

If desired, other active ingredients may be included in the compositions.

In some embodiments, a fusion protein including an anti-apoptotic Bcl-2 family member is useful for enhancing cell survival, enhancing cell proliferation, inhibiting cell death or apoptosis, protecting against cell death, increasing cell activation or promoting cell maturation. Accordingly, compositions including such fusion proteins may, if desired, be combined with any standard therapy typically used to treat a disease or disorder characterized by excess cell death. In one embodiment, the standard therapy is useful for the treatment of cell death or apoptosis associated with hypoxia, ischemia, reperfusion, stroke, Alzheimer's disease, Parkinson's disease, Lou Gehrig's disease, Huntington's chorea, spinal muscular atrophy, spinal cord injury, receipt of a cell, tissue or organ transplantation, receipt of chemotherapy, or receipt of radiation therapy. In particular, for diseases characterized by the death of dopaminergic cells, such as Parkinson's disease, the fusion proteins may be administered in combination with an agent that enhances dopamine production or a dopamine mimetic, with an antidyskinetic agent, such as amantadine or an anti-cholinergic. For ischemic injuries related to the presence of a thrombosis, the fusion protein is administered in combination with an antithrombotic or a thrombolytic agent. Such methods are known to the skilled artisan and described in Remington's Pharmaceutical Sciences by E. W. Martin.

In some embodiments, for the treatment of diseases or disorders affecting the central nervous system, the fusion proteins can be provided in combination with agents that enhance transport across the blood-brain barrier. Such agents are known in the art and are described, for example, by U.S. Patent Publication Nos. 20050027110, 20020068080, and 20030091640. Other compositions and methods that enhance delivery of an active agent across the blood brain barrier are described in the following publications: Batrakova et al., Bioconjug Chem. 2005 July-August; 16(4):793-802; Borlongan et al., Brain Res Bull. 2003 May 15; 60(3):297-306; Kreuter et al., Pharm Res. 2003 March;

20(3):409-16; and Lee et al., J Drug Target. 2002 September; 10(6):463-7. Other methods for enhancing blood-brain barrier transport include the use of agents that permeabilize tight junctions via osmotic disruption or biochemical opening; such agents include RMP-7 (Alkermes), and vasoactive compounds (e.g., histamine). Other agents that enhance transport across the blood-brain barrier enhance transcytosis across the endothelial cells to the underlying brain cells. Enhanced transcytosis can be achieved by increasing endocytosis (i.e. internalisation of small extracellular molecules) using liposomes or nanoparticles loaded with a drug of interest. In alternative embodiments, the fusion protein can be administered in the absence of an agent that enhances transport across the blood-brain barrier.

Alternatively, a fusion protein including an anti-apoptotic Bcl-2 family member can be administered in combination with a chemotherapeutic, such that the fusion protein reduces the toxic effects typically associated with chemotherapy. For example, a patient that receives a chemotherapeutic and a fusion protein is less likely to suffer from side-effects associated with the apoptosis of normal cells (e.g., reduced neutrophil count) than a patient that receives only the chemotherapeutic. A composition of the invention is administered prior to, concurrent with, or following the administration of any one or more of the following: a chemotherapeutic agent, radiation agent, hormonal agent, biological agent, an anti-inflammatory agent, a cancer vaccine adjuvant. Exemplary chemotherapeutic agents include tamoxifen, trastuzamab, raloxifene, doxorubicin, fluorouracil/5-fu, pamidronate disodium, anastrozole, exemestane, cyclophos-phamide, epirubicin, letrozole, toremifene, fulvestrant, fluoxymester-one, trastuzumab, methotrexate, megastrol acetate, docetaxel, paclitaxel, testolactone, aziridine, vinblastine, capecitabine, goselerin acetate, zoledronic acid, taxol, vinblastine, and vincristine.

If necessary to reduce a systemic immune response to the fusion proteins, immunosuppressive therapies can be administered in combination with the fusion proteins including an anti-apoptotic Bcl-2 family member. Examples of immunosuppressive therapies include, but are not limited to, systemic or topical corticosteroids (Suga et al., Ann. Thorac. Surg., 73:1092-7, 2002), cyclosporin A (Fang et al., Hum. Gene Ther., 6:1039-44, 1995), cyclophosphamide (Smith et al., Gene Ther., 3:496-502, 1996), deoxyspergualin (Kaplan et al., Hum. Gene Ther., 8:1095-1104, 1997) and antibodies to T and/or B cells such as anti-CD40 ligand, anti CD4 antibodies, or anti-CD20 antibody (Rituximab) (Manning et al., Hum. Gene Ther., 9:477-85, 1998). Such agents can be administered before, during, or subsequent to administration of the fusion proteins. Such agents can be administered from about 10 mg/week to about 1000 mg/week, from about 40 mg/week to about 700 mg/week, or from about 200 mg/week to about 500 mg/week for 2, 3, 4, 5, 6, or 7 weeks. Courses of treatment can be repeated as necessary if the subject remains responsive (e.g., the symptoms of cancer are static or decreasing).

A "subject" can be a mammal in need of treatment, such as a human or veterinary patient (e.g., rodent, such as a mouse or rat, a cat, dog, cow, horse, sheep, goat, or other livestock). In some embodiments, a "subject" may be a clinical patient, a clinical trial volunteer, an experimental animal, etc. The subject may be suspected of having or at risk for having a condition characterized by cell death, be diagnosed with a condition characterized by cell death, or be a control subject that is confirmed to not have a condition characterized by cell death, as described herein. Diagnostic methods for conditions characterized by cell death and the clinical delineation of such diagnoses are known to those of ordinary skill in the art.

The composition can be a liquid solution, suspension, emulsion, sustained release formulation, or powder, and can be formulated with a pharmaceutically acceptable carrier. The composition can be formulated as a suppository, with traditional binders and carriers such as triglycerides. The term "pharmaceutically-acceptable carrier" refers to a carrier medium or vehicle which does not interfere with the effectiveness of the biological activity of the active ingredients and which is not toxic to the host or subject.

Fusion proteins can be delivered along with a pharmaceutically-acceptable vehicle. In one example, the vehicle may enhance the stability and/or delivery properties. Thus, the disclosure also provides for formulation of the fusion protein with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the fusion proteins. Alternatively, or in addition, the fusion protein formulations can include additives to stabilize the protein in vivo, such as human serum albumin, or other stabilizers for protein therapeutics known in the art. Fusion protein formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions containing one or more fusion proteins can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In some embodiments, the fusion protein is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., Biomacromolecules 7(8):2407-14, 2006).

In some embodiments, a fusion protein including an anti-apoptotic Bcl-2 family member polypeptide (such as a cpIL4-Bcl-xL fusion protein) can be used for inhibiting the apoptosis or promoting the proliferation of dendritic cells during the production of a therapeutic or prophylactic vaccine. In some embodiments, the fusion protein including an anti-apoptotic Bcl-2 family member polypeptide (such as a cpIL4-Bcl-xL fusion protein) is used in combination with a GM-CSF Bcl-xL fusion protein. In general, the vaccine includes a cell (e.g., a dendritic cell) derived from a subject that requires vaccination. In general, the cell is obtained from a biological sample of the subject, such as a blood sample or a bone marrow sample. Preferably, a dendritic cell or dendritic stem cell is obtained from the subject, and the cell is cultured in vitro to obtain a population of dendritic cells. The cultured cells are contacted with an antigen (e.g., a cancer antigen) in the presence of a fusion protein of the invention. Desirably, a dendritic cell contacted with the antigen in the presence of the fusion protein is at reduced risk of apoptosis relative to a dendritic cell contacted in the absence of the fusion protein. Optionally, the contacted cells are expanded in number in vitro. The cells are then re-introduced into the subject where they enhance or elicit an immune response against an antigen of interest (e.g., a cancer antigen). Methods for producing such vaccines are known in the art and are described, for example, by Zhu et al., J Neurooncol. 2005 August; 74(1):9-17; Nair et al., Int. J. Cancer. 1997; 70:706-715; and Fong et al., Annu. Rev. Immunol. 2000; 18:245-273.

Typically vaccines are prepared in an injectable form, either as a liquid solution or as a suspension. Solid forms suitable for injection may also be prepared as emulsions, or with the polypeptides encapsulated in liposomes. The cells are injected in any suitable carrier known in the art. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

Adjuvants are immunostimulating agents that enhance vaccine effectiveness. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Vaccines are administered in a manner compatible with the dose formulation. By an effective amount is meant a single dose, or a vaccine administered in a multiple dose schedule, that is effective for the treatment or prevention of a disease or disorder. Preferably, the dose is effective to inhibit the growth of a neoplasm. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner.

In some embodiments, a fusion protein including an anti-apoptotic Bcl-2 family member polypeptide, as desired, can be used in ex vivo methods. For example, cells (e.g., peripheral blood lymphocytes or purified populations of lymhocytes isolated from a patient and placed or maintained in culture) can be cultured in vitro in culture medium and the contacting step can be affected by adding the IL-4R fusion protein to the culture medium. The culture step can include further steps in which the cells are stimulated or treated with other agents, e.g., to stimulate or reduce proliferation, or to expand or deplete a population of cells (e.g., $T_H2$ cells). The cells are then administered to the patient.

The pharmaceutical compositions described herein include one or more fusion proteins in an amount effective to achieve the intended purpose. Typically, compositions including a fusion protein containing an anti-apoptotic Bcl-2 family member are administered to a patient already suffering from a disease, disorder or condition characterized by cell death, or at risk for such a disease, disorder or condition, in an amount sufficient to cure or at least partially arrest a symptom associated with cell death or enhance cell growth, survival, activation or maturation.

The skilled person will therefore recognize that the dosage to be administered is not subject to defined limits. Prior to administration for therapeutic purposes, the dosage of the fusion protein may need to be modified or adapted for the particular purpose, for example the concentration of fusion protein needed for whole body administration may differ from that used for local administration. Similarly, the toxicity of the therapeutic may change depending upon the mode of administration and overall composition being used (e.g., buffer, diluent, additional chemotherapeutic, etc.).

An "effective amount" of a pharmaceutical composition according to the invention includes a therapeutically effective amount or a prophylactically effective amount. A "therapeutically effective amount" refers to an amount of the fusion protein effective, at dosages and for periods of time necessary, that ameliorates the symptoms of the disease, disorder or condition to be treated. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the fusion protein are outweighed by the therapeutically beneficial effects. Determination of a therapeutically effective dose of a compound is well within the capability of those skilled in the art. For example, the therapeutically effective dose can be estimated initially either in cell culture assays, or in animal models, such as those described herein. A "prophylactically effective amount" refers to an amount of the fusion protein effective, at dosages and for periods of time necessary, that achieves the desired prophylactic result, such as delay in onset of symptoms of a neurological disorder or continued remission of a cancer. Animal models can also be used to determine the appropriate concentration range and route of administration. Such information can then be used to determine useful doses and routes for administration in other animals, including humans, using standard methods known in those of ordinary skill in the art.

Concentration of the fusion protein in the final formulation can be at least 0.1 mg/mL, such as at least 1 ng/mL or at least 1 ug/mL or at least 1 mg/mL. For example, the concentration in the final formulation can be between about 0.01 ug/mL and about 1,000 ug/mL. In one example, the concentration in the final formulation is between about 0.01 mg/mL and about 100 mg/mL.

In some embodiments, a fusion protein including an anti-apoptotic Bcl-2 family protein, or fragment thereof, is administered at concentrations ranging from about 10 ng/mL to about 10,000 ng/mL, or any value therebetween, such as about 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1500 ng/mL, 2000 ng/mL, 2500 ng/mL, 3000 ng/mL, 3500 ng/mL, 4000 ng/mL, 4500 ng/mL, 5000 ng/mL, 5500 ng/mL, 6000 ng/mL, 6500 ng/mL, 7000 ng/mL, 7500 ng/mL, 8000 ng/mL, 8500 ng/mL, 9000 ng/mL, 9500 ng/mL, or 10000 ng/mL.

However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope in any way. In some instances dosage levels below the lower limit of the aforesaid range may be more than adequate, while in other cases still larger doses may be employed without causing harmful side effects, for example, by first dividing the larger dose into several smaller doses for administration throughout the day.

One of ordinary skill in the art will appreciate that the dosage will depend, among other things, upon the type of fusion protein being used and the type of disorder or condition being treated.

In general, the fusion proteins according to the present disclosure contain substantially human sequences and are therefore less antigenic than, for example, immunotoxins or other molecules that contain non-human sequences. In some embodiments, the fusion proteins according to the present disclosure contain at least 80%, for example, 80%, 85%, 90%, 95%, 96%, 97%, 98%, 99% or 100% human sequences. In some embodiments, the fusion proteins according to the present disclosure can be administered at substantially lower doses than for example, immunotoxins, or native IL-4R binding protein, such as IL-4 or IL-13.

In some embodiments, the fusion proteins may elicit some level of antibody response when administered to a subject, which in some cases may lead to undesirable side effects. Therefore, if necessary, the antigenicity of the fusion proteins can be assessed as known in the art and/or described herein. For example, in vivo toxic effects of the fusion proteins can be evaluated by measuring their effect on animal body weight during treatment and by performing hematological profiles and liver enzyme analysis after the animal has been killed. The general toxicity of the fusion proteins can be tested according to methods known in the art. For example, the overall systemic toxicity of the fusion proteins can be tested by determining the dose that kills 100% of mice (i.e. $LD_{100}$) or kills 50% of mice (i.e. $LD_{50}$) following a single intravenous injection. Doses that are at least about 2, 5, or 10-fold less than the $LD_{100}$ or $LD_{50}$ can be selected for administration into other mammals, such as a human.

The kinetics and magnitude of the antibody response to the fusion proteins described herein can be determined, for example, in immunocompetent mice and can be used to facilitate the development of a dosing regimen that can be used in an immunocompetent human. Immunocompetent mice such as the strain C57-BL6 are administered intravenous doses of fusion protein. The mice are killed at varying intervals (e.g. following single dose, following multiple doses) and serum obtained. An ELISA-based assay can be used to detect the presence of anti-fusion protein antibodies.

Serum samples from mice can be assessed for the presence of anti-fusion protein antibodies as known in the art. As another example, epitope mapping can also be used to determine antigenicity of proteins as described in Stickler, et al., J. Immunotherapy, 23:654-660, 2000. Briefly, immune cells known as dendritic cells and CD4+ T cells are isolated from the blood of community donors who have not been exposed to the protein of interest. Small synthetic peptides spanning the length of the protein are then added to the cells in culture. Proliferation in response to the presence of a particular peptide suggests that a T cell epitope is encompassed in the sequence. This peptide sequence can subsequently be deleted or modified in the fusion protein thereby reducing its antigenicity.

Therapeutic efficacy and toxicity can also be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

For administration to an animal, the pharmaceutical compositions can be formulated for administration by a variety of routes. For example, the compositions can be formulated for topical, rectal or parenteral administration or for administration by inhalation or spray. The term parenteral as used herein includes subcutaneous injections, intravenous, intramuscular, intrathecal, intrasternal injection or infusion techniques. Convection enhanced delivery can also be used to administer the fusion protein.

Fusion proteins including an anti-apoptotis Bcl-2 family member can be used in enhancing cell survival or proliferation in the central nervous system (CNS). When the site of delivery is the brain, the fusion protein must be capable of being delivered to the brain. The blood-brain barrier limits the uptake of many therapeutic agents into the brain and spinal cord from the general circulation. Molecules which cross the blood-brain barrier use two main mechanisms: free diffusion and facilitated transport. Because of the presence of the blood-brain barrier, attaining beneficial concentrations of a given fusion protein in the CNS may require the use of specific drug delivery strategies. Delivery of fusion proteins to the CNS can be achieved by several methods.

One method relies on neurosurgical techniques. For instance, fusion proteins can be delivered by direct physical introduction into the CNS, such as intraventricular, intralesional, or intrathecal injection. Intraventricular injection can be facilitated by an intraventricular catheter, for example, attached to a reservoir, such as an Ommaya reservoir. Methods of introduction are also provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents, such as leukotrienes or by convention enhanced delivery by catheter (CED). Further, it may be desirable to administer the compositions locally to the area in need of treatment; this can be achieved, for example, by local infusion during surgery, by injection, by means of a catheter, or by means of an implant, the implant being of a porous, non-porous, or gelatinous material, including membranes, such as silastic membranes, or fibers. A suitable membrane is Gliadel® (Eisai Inc.).

The in vivo or in vitro expression of a fusion protein including an anti-apoptotis Bcl-2 family member (e.g., a IL-4R binding protein-Bcl-XL fusion protein), or fragment thereof is another therapeutic approach for promoting the survival or proliferation of a cell at risk of undergoing cell death. Nucleic acid molecules encoding such fusion proteins can be delivered to cells of a subject that are at risk for apoptosis. The expression of a fusion protein in a cell promotes proliferation, prevents apoptosis, or reduces the risk of apoptosis in that cell or in a target cell or tissue. The nucleic acid molecules must be delivered to the cells of a subject in a form in which they can be taken up so that therapeutically effective levels of the fusion protein can be produced. Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a fusion protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer a chimeric polynucleotide to a target cell, tissue, or systemically.

Non-viral approaches can also be employed for the introduction of a therapeutic to a cell requiring modulation of cell death (e.g., a cell of a patient). For example, a nucleic acid molecule can be introduced into a cell by administering the nucleic acid molecule in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of a fusion protein into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The present invention will be further illustrated in the following examples.

EXAMPLES

Example 1 cpIL-4-BclxL fusion protein was prepared using standard techniques, using commercially available recombinant human IL-4 as a reference. The effect of recombinant human IL-4 (rhIL-4) and cpIL-4-Ub-BclxL on neural cell survival, after insult with GSNO or STS, was determined. The results of a number of tests indicated that the fusion protein was more protective.

Figure 1B:
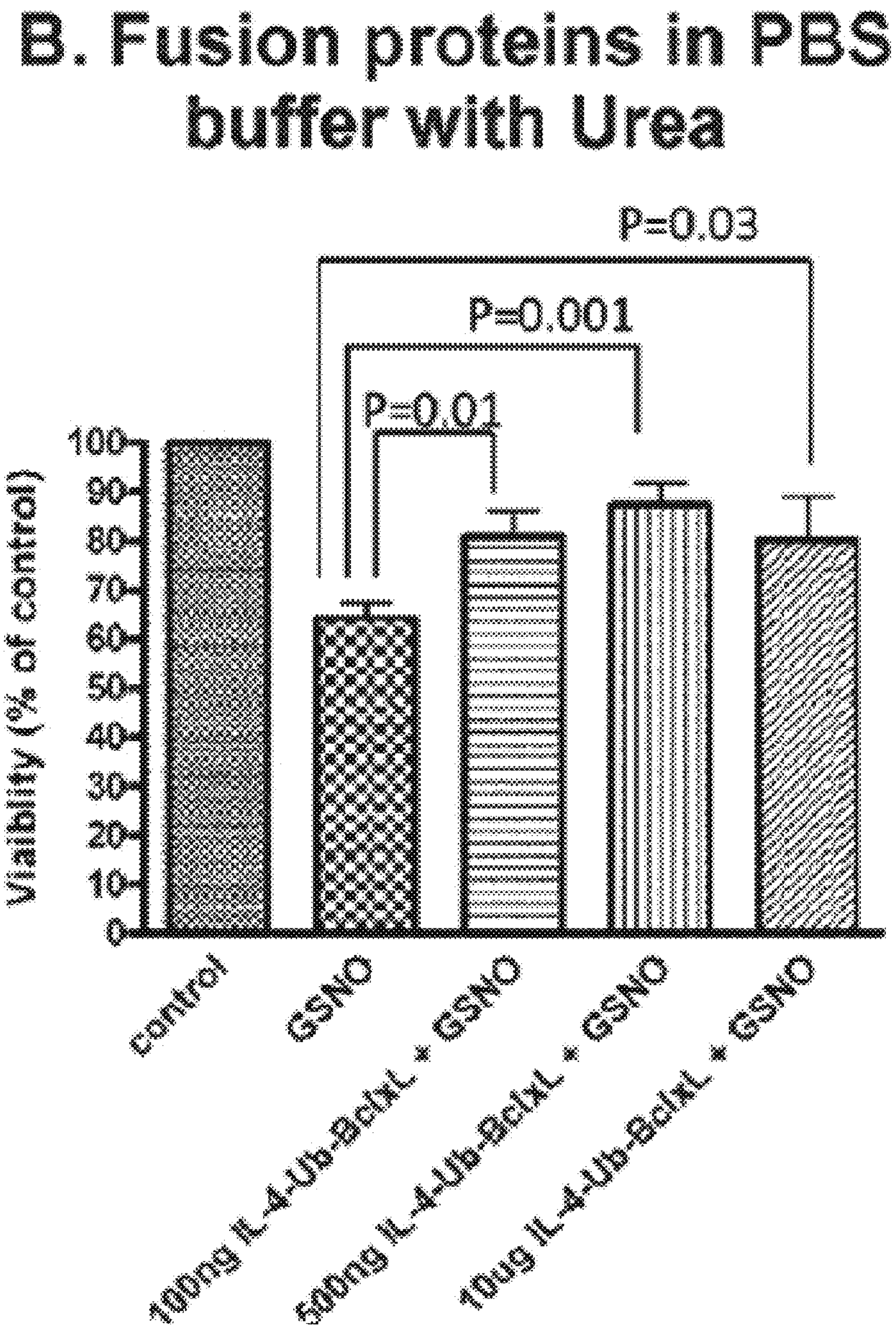
Figure 1C:
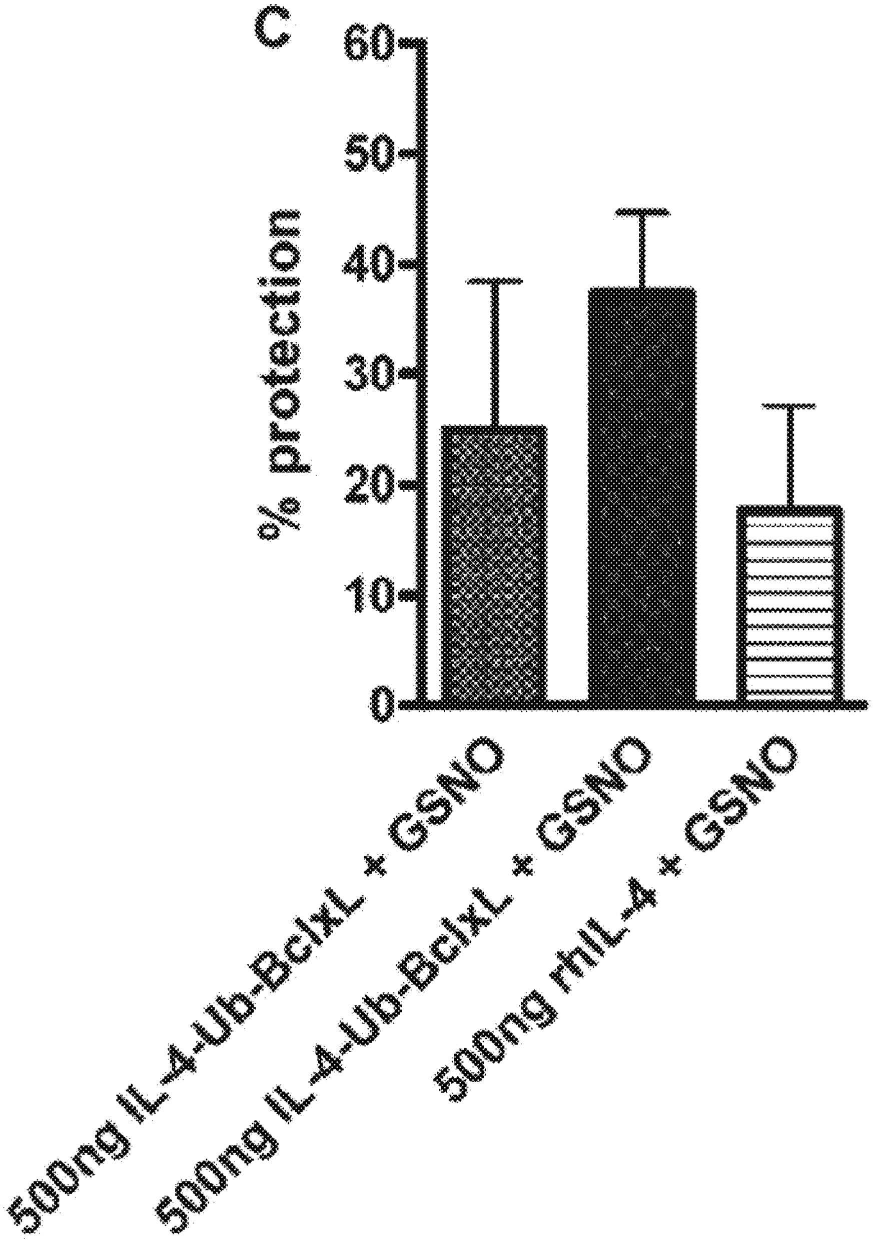

In one test, SH-SY5Y cells were incubated with fusions proteins or recombinant IL-4 (rhIL-4) for 2 hours in serum free medium. GSNO (0.25 mM) was added in DMEM and 10% serum for 22 hours. The viability of the cells was assessed by CFDA assay in 2-3 experiments. The fusions proteins were tested in Tris buffer with Tween 80 (FIG. 1A) and in PBS buffer with Urea (FIG. 1B). cpIL-4-Ub-BclxL (500 ng) increased cell survival after GSNO treatment by about 25-40%, while rhIL-4 (500 ng) increased cell viability by only about 15% (FIG. 1C).

Figure 2A:
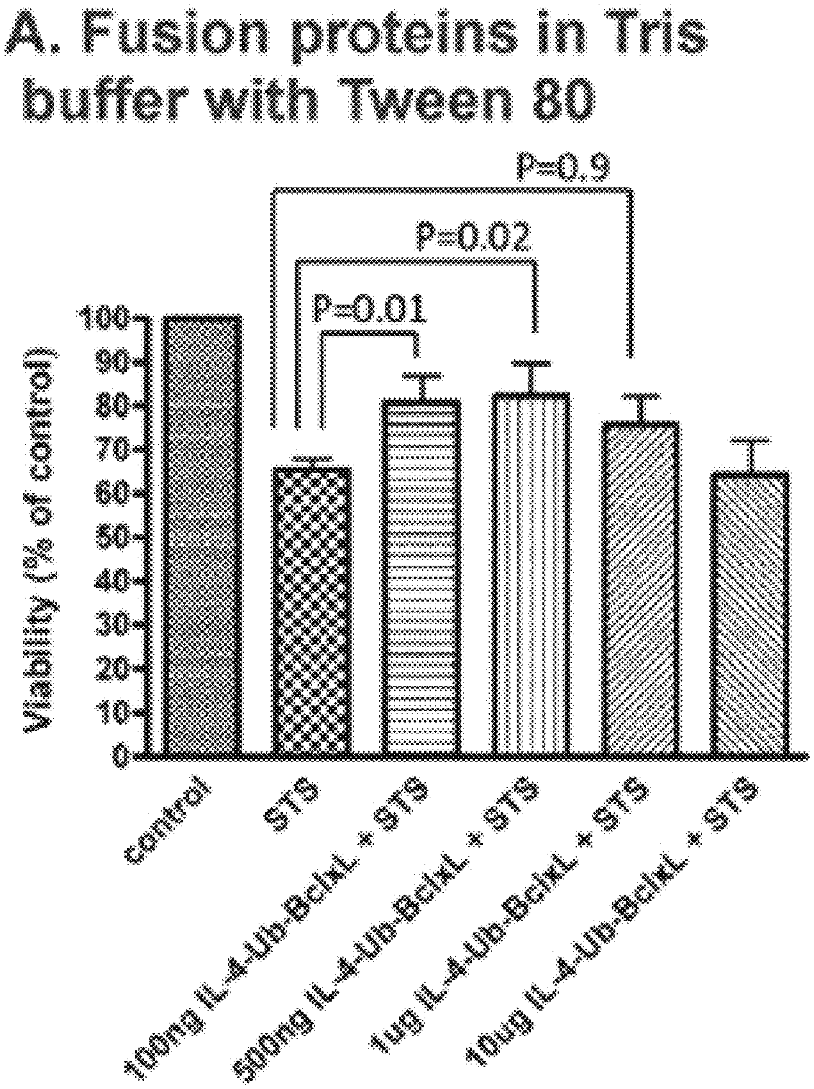
FIG. 2 is a graph showing the effect of cpIL-4-Ub-BclxL or rhIL-4 on neural cell (SH-SY5Y) survival after insult with STS.
Figure 2B:
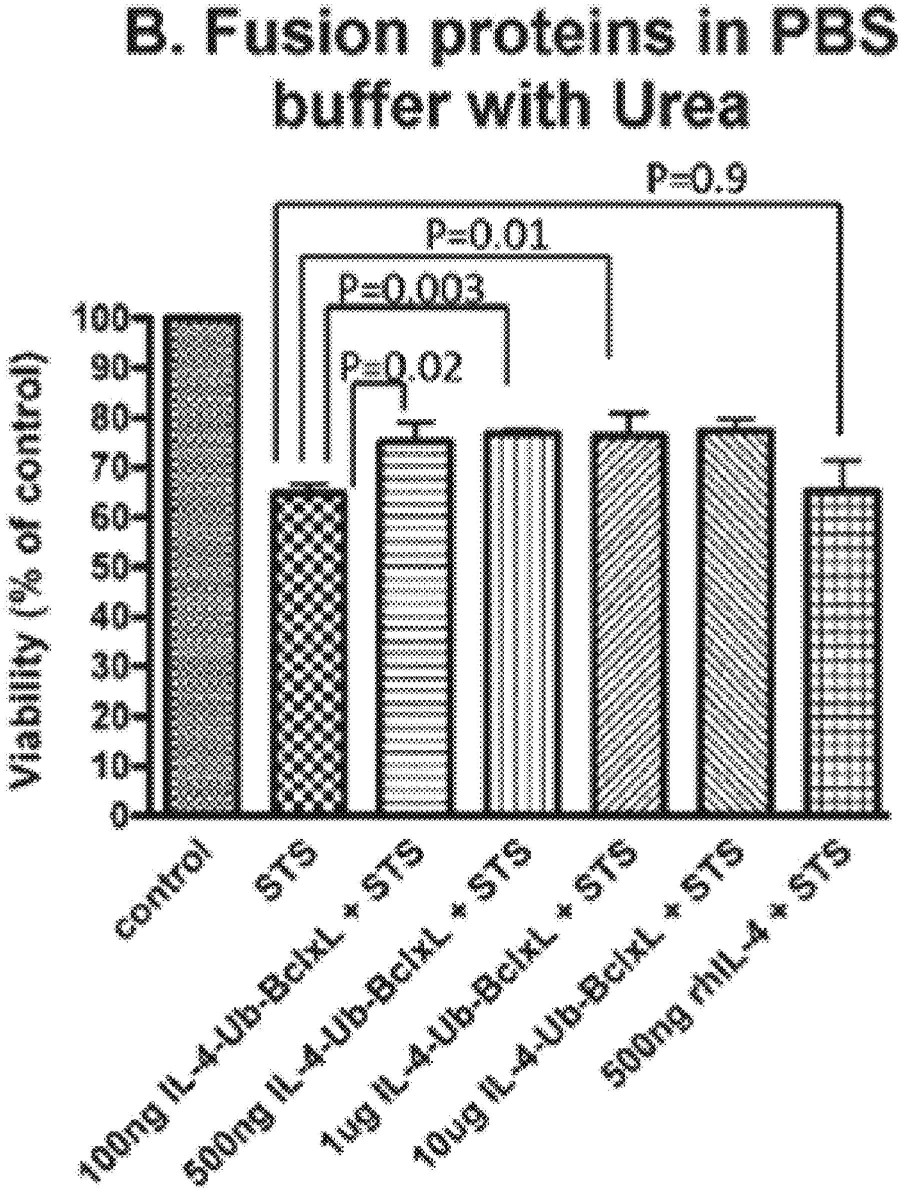
Figure 2C:
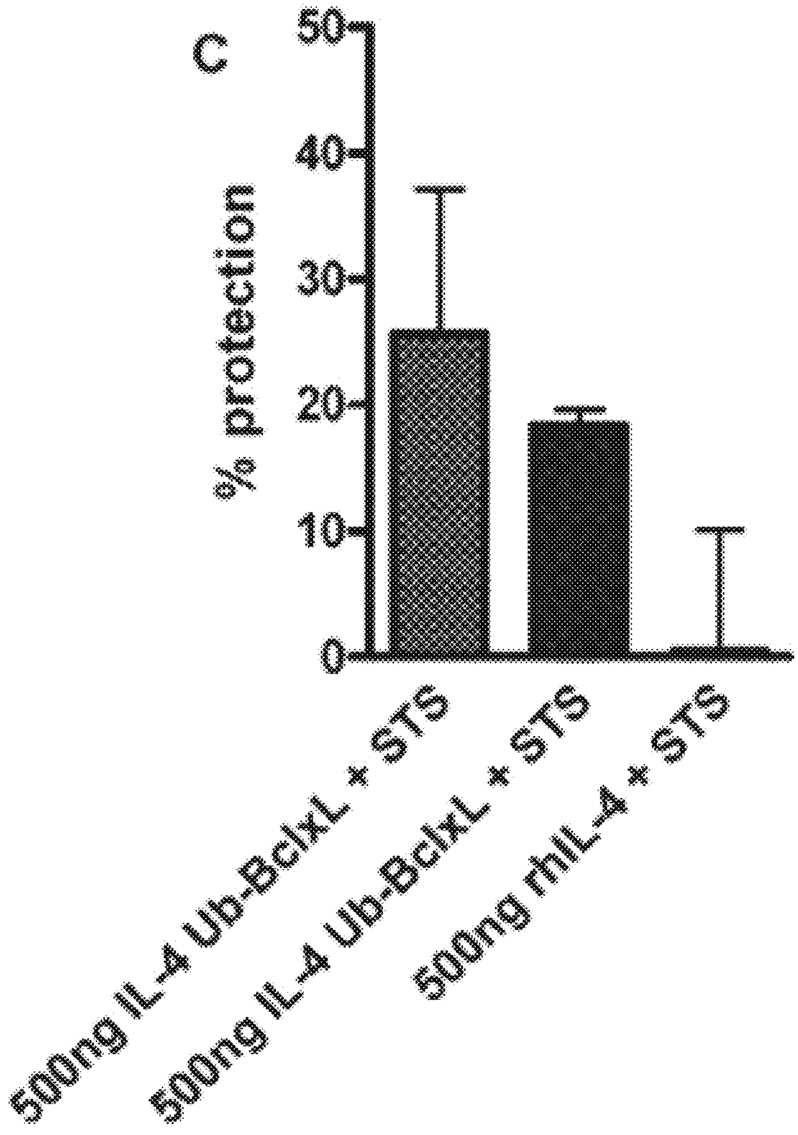

To test the effect of the fusion proteins on neural cell survival in response to STS-induced cell death, SH-SY5Y cells were incubated with the fusion proteins or recombinant IL-4 (rhIL-4) for 2 hours in serum free medium. STS (50 nM) was added in DMEM and 10% serum and incubated for 22 hours. Cell viability was assessed by CFDA assay in 2 experiments. The fusions proteins were tested in Tris buffer with Tween 80 (FIG. 2A) and in PBS buffer with Urea (FIG. 2B). cpIL-4-Ub-BclxL (500 ng) increased cell survival after STS treatment by about 20-25%, while rhIL-4 (500 ng) showed no significant protection against STS-induced cell death (FIG. 2C).

Example 2

Figure 3:
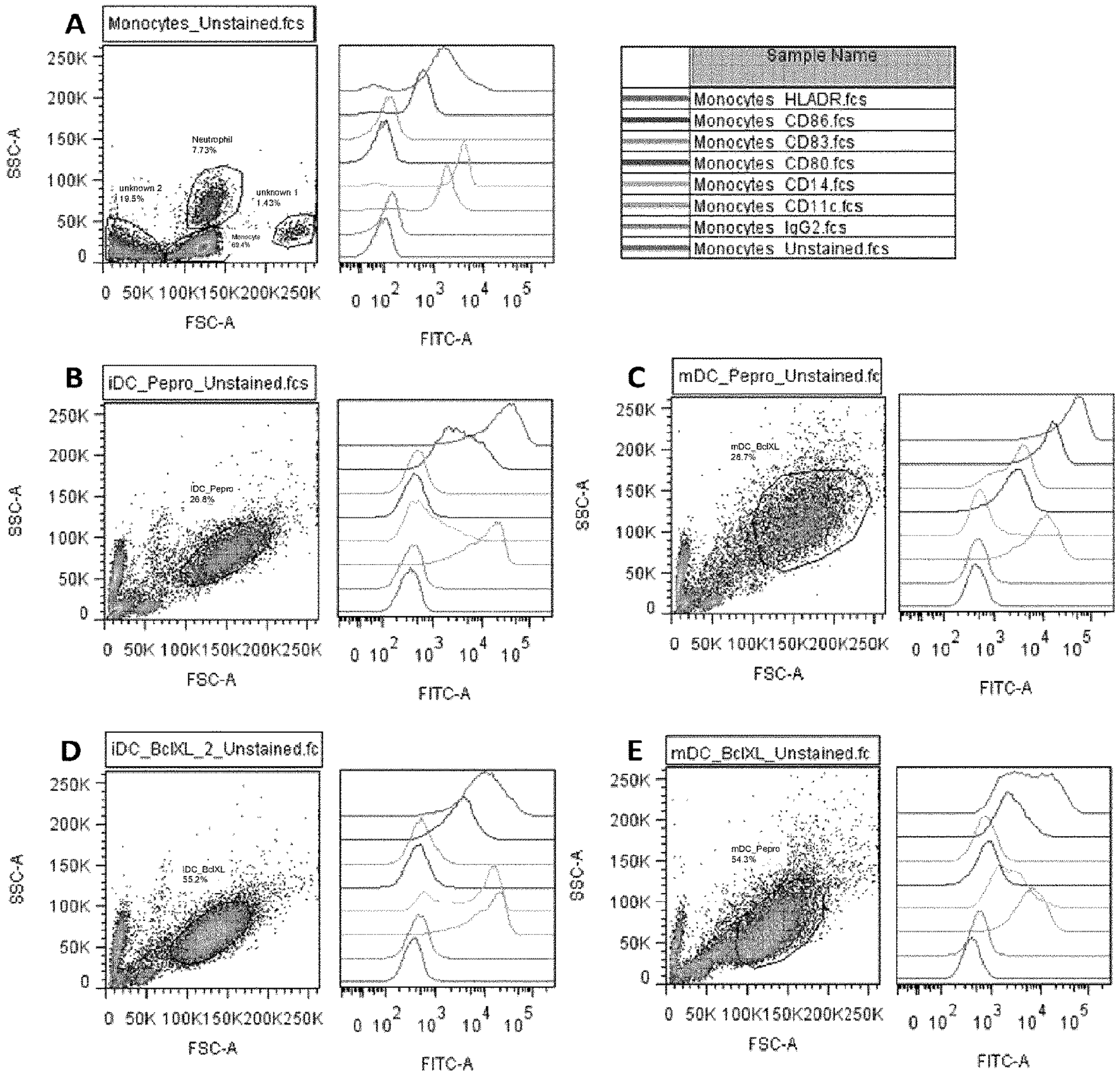
FIGS. 3A-E are graphs showing the effect of GM-CSF-Bcl-XL and cpIL-4-Bcl-XL on human dendritic cell derivation.

Human dendritic cells (DCs) were generated by culturing peripheral blood derived monocytes in granulocyte-macrophage colony-stimulating factor (GM-CSF) and interleukin-4 (IL-4) (FIG. 3A), resulting into immature DCs (iDCs) (FIG. 3B), which are further matured to mature DCs (mDCs) (FIG. 3C) with additional factors and cytokines, using standard techniques. When GM-CSF-Bcl-$X_L$ and cpIL-4-Bcl-$X_L$ were used to generate human DCs (FIG. 3D), the yield of iDCs was 1.8 times greater than DCs generated by using wild type IL-4 and GM-CSF alone. The phenotype of iDCs generated by both conditions was similar. When iDCs were matured to mDCs (FIG. 3E) the yield of mDCs remained higher using Bcl-$X_L$ fused cytokines compared to native cytokines. Gene expression profiling using whole genome transcriptome microarrays (~35,000 probes) to characterize DCs generated by Bcl-$X_L$ cytokines, showed that when monocytes differentiate to iDCs, they dramatically increase gene expression related to transcript regulators, transporters, transmembrane receptors, peptidase and phosphatase and when iDCs differentiate to mDCs, cytokine and chemokine encoded genes and Th1 rather than Th2 attractants were up-regulated. Despite these changes, there were no statistical significant differences in gene expression (criteria FDR 0.01 and fold change 1.5) between Bcl-$X_L$-iDCs and iDCs and between Bcl-$X_L$-mDC and mDC. These results indicate that Bcl-$X_L$ cytokines generated DCs have higher yields without any difference in phenotype or overall gene expression profile and thus useful in cancer therapy.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A fusion protein comprising an interleukin-4 (IL-4) receptor binding protein and an anti-apoptotic Bcl-2 family polypeptide, wherein the fusion comprises the amino acid sequence of any one of SEQ ID NOs:18 and 20-24.

2. The fusion protein of claim 1, wherein the fusion protein comprises the amino acid sequence of SEQ ID NO:18.

3. The fusion protein of claim 1, wherein the fusion protein comprises the amino acid sequence of SEQ ID NO:20.

4. The fusion protein of claim 1, wherein the fusion protein comprises the amino acid sequence of SEQ ID NO:21.

5. The fusion protein of claim 1, wherein the fusion protein comprises the amino acid sequence of SEQ ID NO:22.

6. The fusion protein of claim 1, wherein the fusion protein comprises the amino acid sequence of SEQ ID NO:23.

7. The fusion protein of claim 1, wherein the fusion protein comprises the amino acid sequence of SEQ ID NO:24.

8. A composition comprising the fusion protein of claim 1 and further comprising a GM-CSF-Bcl-XL fusion protein.

9. A pharmaceutical composition comprising the fusion protein of claim 1.

10. A nucleic acid molecule comprising the nucleic acid sequence of any one of SEQ ID NOs: 30 or 31.

11. The nucleic acid molecule of claim 10, wherein the nucleic acid molecule comprises the nucleic acid sequence of SEQ ID NO:30.

12. A vector comprising the nucleic acid molecule of claim 11.

13. An isolated or cultured host cell comprising the vector of claim 12.

14. The nucleic acid molecule of claim 10, wherein the nucleic acid molecule comprises the nucleic acid sequence of SEQ ID NO:31.

15. A vector comprising the nucleic acid molecule of claim 14.

16. An isolated or cultured host cell comprising the vector of claim 15.

* * * * *